United States Patent
Zhang et al.

(10) Patent No.: US 11,993,603 B2
(45) Date of Patent: May 28, 2024

(54) PREPARATION FOR 6-AMINO-1H-PYRAZOLO[3,4-d] PYRIMIDINE-BASED JAK KINASE INHIBITOR AND APPLICATION THEREOF

(71) Applicants: INSTITUTE OF MATERIA MEDICA, CHINESE ACADEMY OF MEDICAL SCIENCES & PEKING UNION MEDICAL COLLEGE, Nanjing (CN); CHINA PHARMACEUTICAL UNIVERSITY, Beijing (CN)

(72) Inventors: Tiantai Zhang, Nanjing (CN); Dayong Zhang, Beijing (CN); Chengjuan Chen, Nanjing (CN); Yuan Yin, Beijing (CN); Runan Yu, Nanjing (CN); Lei Shu, Nanjing (CN)

(73) Assignees: INSTITUTE OF MATERIA MEDICA, CHINESE ACADEMY OF MEDICAL SCIENCES & PEKING UNION MEDICAL COLLEGE, Beijing (CN); CHINA PARMACEUTICAL UNIVERSITY, Nanjing (CN)

( * ) Notice: Subject to any disclaimer, the term of this patent is extended or adjusted under 35 U.S.C. 154(b) by 623 days.

(21) Appl. No.: 17/275,209

(22) PCT Filed: Sep. 5, 2019

(86) PCT No.: PCT/CN2019/104494
§ 371 (c)(1),
(2) Date: Mar. 11, 2021

(87) PCT Pub. No.: WO2020/052489
PCT Pub. Date: Mar. 19, 2020

(65) Prior Publication Data
US 2022/0048914 A1    Feb. 17, 2022

(30) Foreign Application Priority Data
Sep. 11, 2018  (CN) .................. 201811078582.X

(51) Int. Cl.
*C07D 487/04* (2006.01)
*A61P 37/06* (2006.01)

(52) U.S. Cl.
CPC ............ *C07D 487/04* (2013.01); *A61P 37/06* (2018.01)

(58) Field of Classification Search
CPC ......... A61P 37/06; A61P 37/02; C07D 487/04
See application file for complete search history.

(56) References Cited

FOREIGN PATENT DOCUMENTS

| WO | WO-2011048082 A1 * | 4/2011 | ........... C07D 487/04 |
| WO | WO-2015164614 A1 * | 10/2015 | ........... C07D 239/47 |

OTHER PUBLICATIONS

Richard B. Silverman. The Organic Chemistry of Drug Design and Drug Action, Book, 2004, pp. 25-34 (Year: 2004).*
William Damsky, et al. The emerging role of Janus kinase inhibitors in the treatment of autoimmune and inflammatory diseases. Journal of Allergy and Clinical Immunology. vol. 147, Issue 3, Mar. 2021, pp. 814-826 (Year: 2020).*
Jesse Klein. Can a person prevent multiple sclerosis? Medical News Today. pp. 1-9. Apr. 2020. (Year: 2020).*
Tatjana Welzel, et al. Management of Monogenic IL-1 Mediated Autoinflammatory Diseases in Childhood. Front. Immunol., vol. 12. Mar. 18, 2021. pp. 1-10. (Year: 2021).*

* cited by examiner

*Primary Examiner* — Noble E Jarrell
*Assistant Examiner* — Richard Grant Peckham
(74) *Attorney, Agent, or Firm* — CBM PATENT CONSULTING, LLC

(57) ABSTRACT

A medicament with excellent JAK kinase (Janus Kinase) inhibitory activity can be used to prevent, treat and/or improve an autoimmune disease (e.g., psoriasis, rheumatoid arthritis, inflammatory bowel disease, Sjogren's syndrome, Behcet's disease, multiple sclerosis, systemic lupus erythematosus and the like). The present invention also provides a pharmaceutically acceptable composition containing the compound and a method for preparing these compounds.

6 Claims, No Drawings

PREPARATION FOR 6-AMINO-1H-PYRAZOLO[3,4-d] PYRIMIDINE-BASED JAK KINASE INHIBITOR AND APPLICATION THEREOF

FIELD OF TECHNOLOGY

The present disclosure relates to use of a heterocyclic compound having JAK kinase inhibiting effect as a medicament for preventing, treating and/or improving an autoimmune disease (e.g., psoriasis, rheumatoid arthritis, inflammatory enteritis disease, Sjogren's syndrome, Behcet's disease, multiple sclerosis, and systemic lupus erythematosus), and relates to a pharmaceutical composition including the same, and the like.

BACKGROUND

JAK kinase (Janus Kinase) and the effectors, signal transducers and activators of transcription proteins (STATs) downstream thereof form an important cytokine signal transduction pathway, namely, a JAK-STAT pathway (Science, 1994, 264: 1415-1421). The pathway is an intracellular signal transduction pathway closely related to cytokines. Researches show that the passage can be activated by multiple cytokines, growth factors and receptors; and participates in lots of important biological process, such as cell proliferation, differentiation, apoptosis, angiogenesis and immunoregulation (World J Gastroenterol, 2007, 13: 6478-6491).

JAK kinase family plays an important role in cytokine-dependent regulation and growth as well as cells associated with immune response. JAK family is non-receptor tyrosine kinases present in cells; and the family contains 4 major members in mammal bodies: JAK-1 (also known as janus kinase 1), JAK-2 (also known as janus kinase 2), JAK-3 (also known as janus kinase 3) and TYK-2 (also known as tyrosine kinase 2). JAK-1, JAK-2 and TYK-2 are extensively expressed in various histocytes, while JAK3 is mainly expressed in hematopoietic cells. JAK-STAT signal pathway is a signal transduction pathway stimulated by multiple cytokine receptors. JAK kinase mediates the signal transduction of the majority of intracellular cytokines (Prog Med Chem, 2013, 52: 153-223), such as, interleukins (IL), interferons (IFN), somatotropin (GH), prolactin (PRL), thrombopoietin (TPO), platelet-derived growth factors (PDGF) and epidermal growth factors (EGF). Moreover, different receptors can activate different kinds of subtype JAK kinases, thus exhibiting differentiated biological functions (Immunol Rev, 2008, 223: 132-142, Nat Immunol, 2009, 10: 356-360). JAK-3 is combined with a γ chain ($\gamma_c$) in I-type cytokine receptor complexes, such as, IL-2, IL-4, IL-7, IL-9, IL-15 and IL-21 to regulate cell signal transduction. Mutation or deletion of JAK3 often results in serious consequences, for example, severe combined immunodeficiency disease (SCID); analysis on hereditary SCID patients have revealed that 7%-14% patients carry homozygous mutations of a JAK-3 gene, and these mutations may lead to the change of JAK-3 expression or functions (Blood, 1996, 88: 817-823), which is manifested as the decrease of T cells and natural killer cells (NKs), function loss of B cells and other immune-restricted symptoms (Chin J New Drug, 2015, 24: 39-45). Moreover, numerous types of interleukins secreted by lymphocytes have pro-inflammatory and anti-inflammatory effects, and play important roles in the damage repair of cartilage tissues; JAK-3 is highly expressed in lymphocytes and plays an important role in JAK-STAT signal transmission and lymphocyte function regulation. Therefore, JAK3 is a vital factor in the attack and treatment of rheumatoid arthritis. Meanwhile, due to the extensive regulating effect of the JAK-STAT signal pathway, the occurrence of psoriasis, ankylosing spondylitis, xerophthalmia, Crohn's disease and other lots of diseases also involves in the effects of JAK-3. Thus, it is easy to see the key function of JAK-3, as a signal transmission member, in the occurrence of diseases (Journal of Allergy and Clinical TmmurmLogy 127, 3, 701-721. e70(2011), Cytokine & Growth Factor Reviews 19, 41-52(2008), Invest Ophthalmol Vis Sci. 2008Jul; 49 (7):3058-3064, Ann Rheum Dis. 2010 Jul; 69 (7): 1325-1328). Thus, it can be seen that JAK kinase inhibitor is a potential therapeutic drug for various kinds of autoimmune diseases.

Directed to ATP binding sites on JAK, the research group always makes continuous exploration and aims at developing a high-activity and high-selectivity JAK inhibitor to competitively inhibit the binding of ATP to ATP binding sites on JAK, block out ATP hydrolysis and disturb JAKs phosphorylation process, thus preventing the JAKs activation and cutting off its signal transmission to STATs, thereby resulting in the failure of regulating and controlling the expression of genes in cell nucleus and achieving the purpose of blocking the JAK-STAT signal pathway.

Through the discussion on the structure-function relationship of the compound, the research group develops preparation of a novel 6-amino-1H-pyrazolo[3,4-d]pyrimidines JAK kinase inhibitor and use thereof now; where the compound in example 1 is a JAK-3 inhibitor lead compound showing high inhibitory activity (IC50=0.085 nM) and high selective activity (JAK-1/JAK-3 and TYK-2/JAK-3 are greater than 58823; JAK-2/JAK-3=36494); and the compound in example 1 has a simple synthetic route and high implementation.

Examples of a compound having a similar structure with the compound described in the description are as follows:

(1) a compound represented by the following formula:

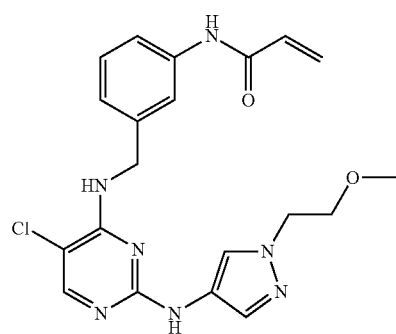 [SMILES: C=CC(=O)Nc1cccc(CNc2nc(Nc3cnn(CCOC)c3)ncc2Cl)c1]

(Non-Patent Document 1);

(2) a compound represented by the following formula:

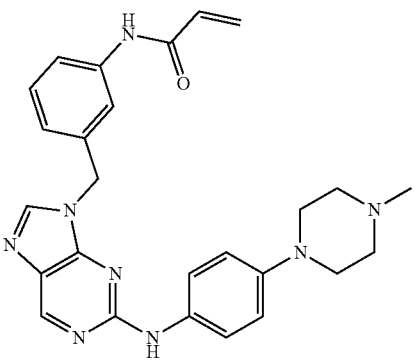 [SMILES: C=CC(=O)Nc1cccc(Cn2cnc3cnc(Nc4ccc(N5CCN(C)CC5)cc4)nc32)c1]

(Non-Patent Document 1);
(3) a compound represented by the following formula:

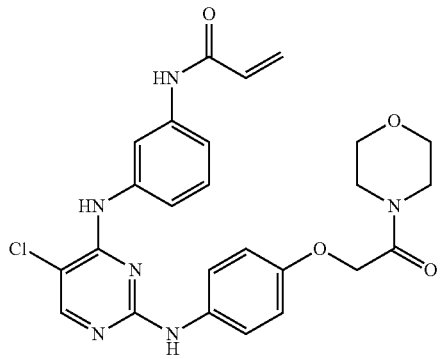 [SMILES: C=CC(=O)Nc1cccc(Nc2nc(Nc3ccc(OCC(=O)N4CCOCC4)cc3)ncc2Cl)c1]

(Non-Patent Document 2).

DOCUMENT LIST

Non-Patent Documents

[Non-Patent Document 1] Tan L, Akahane K, McNally R, et al. Development of selective covalent Janus kinase 3 inhibitors[J]. Journal of medicinal chemistry, 2015, 58(16): 6589-6606.

[Non-Patent Document 2] Ge Y, Wang C, Song S, et al. Identification of highly potent BTK and JAK3 dual inhibitors with improved activity for the treatment of B-cell lymphoma[J]. European journal of medicinal chemistry, 2018, 143: 1847-1857.

SUMMARY OF THE INVENTION

Problem to be Solved by the Present Disclosure

An objective of the present disclosure is to provide a medicament with excellent selective JAK kinase (Janus Kinase) inhibitory activity for preventing, treating and/or improving an autoimmune disease (e.g., psoriasis, rheumatoid arthritis, inflammatory bowel disease, Sjogren's syndrome, Behcet's disease, multiple sclerosis, systemic lupus erythematosus and the like).

Method to Solve the Problem

To attempt to solve the above problem, the inventor has performed an in-depth study and found that the compound (I) represented by the following formula has an excellent JAK-3 inhibitory activity, thus achieving the present disclosure.

Accordingly, the present disclosure provides the following contents.

[1] A compound represented by Formula (I) or a pharmaceutically acceptable salt thereof:

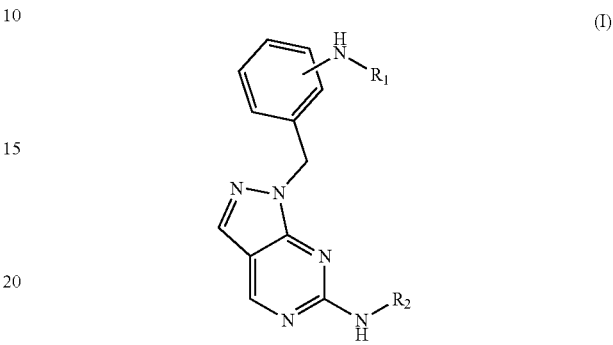

where:
  $R_1$ is independently selected from hydrogen atom, halogen, cyano, hydroxyl,

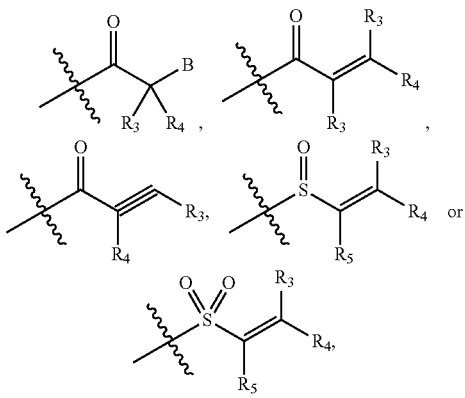

where
  B is independently selected from hydrogen atom, halogen, cyano, hydroxyl;
  $R_3$, $R_4$ and $R_5$ are independently selected from hydrogen atom, halogen, cyano, hydroxyl, substituted or unsubstituted $C_{1-6}$ alkyl or substituted or unsubstituted $C_{1-6}$ heteroalkyl or substituted or unsubstituted $C_{3-8}$ cycloalkyl, substituted or unsubstituted $C_{3-8}$ heterocycloalkyl, substituted or unsubstituted 5-, 6-, 7- or 8-membered aryl, substituted or unsubstituted 5-, 6-, 7- or 8-membered heteroaryl;
  $R_2$ is phenyl, naphthyl, aromatic 5- to 6-membered heterocyclyl, or aromatic 9- to 11-membered heterobicyclyl, where a ring is optionally substituted by one or more $R^1$ groups;
  each $R^1$ is independently halogen, CN, $C(O)OR^2$, $OR^2$, $C(O)R^2$, $S(O)_2R^2$, $S(O)R^2$, $NO_2$, $OC(O)R^2$, $C_{1-6}$ alkyl, $C_{2-6}$ alkenyl or $C_{2-6}$ alkynyl, where the $C_{1-6}$ alkyl, $C_{2-6}$ alkenyl and $C_{2-6}$ alkynyl are optionally substituted by one or more $R^3$ groups which are identical or different;
  $R^2$ is independently selected from H, $C_{1-6}$ alkyl, $C_{2-6}$ alkenyl or $C_{2-6}$ alkynyl, where the $C_{1-6}$ alkyl, $C_{2-6}$ alkenyl or $C_{2-6}$ alkynyl are optionally substituted by one or more $R^3$ groups which are identical or different;

$R^3$ is halogen, CN, C(O)OR$^4$, OR$^4$, C(O)R$^4$, S(O)$_2$R$^4$, S(O)R$^4$, NO$_2$, OC(O)R$^4$;

$R^4$ is independently selected from H, $C_{1-6}$ alkyl, $C_{2-6}$ alkenyl or $C_{2-6}$ alkynyl, where $C_{1-6}$ alkyl, $C_{2-6}$ alkenyl and $C_{2-6}$ alkynyl are optionally substituted by one or more halogens which are identical or different.

[2] The compound or salt thereof of the above [1], where $R_1$ is
(1) hydrogen atom,
(2) halogen atom,
(3) cyano,
(4) acrylyl,
(5) 2-cyanoacetyl,
(6) $C_{1-6}$ alkyl optionally substituted by 1 to 3 substituents selected from: (a) hydrogen atom, (b) halogen atom, (c) hydroxyl, (d) $C_{1-6}$ alkoxy, (e) $C_{3-8}$ cycloalkyl, (f) $C_{1-6}$ alkyl-carbonyl mono- or di-substituted amino,
(7) $C_{2-7}$ alkenyl optionally substituted by 1 to 3 substituents selected from: (a) hydrogen atom, (b) halogen atom, (c) optionally substituted $C_{1-6}$ alkyl,
(8) $C_{2-7}$ alkynyl optionally substituted by 1 to 3 substituents selected from: (a) hydrogen atom, (b) halogen atom, (c) optionally substituted $C_{1-6}$ alkyl,
(9) $C_{3-10}$ cycloalkyl optionally substituted by 1 to 3 substituents selected from: (a) halogen atom, (b) $C_{1-6}$ alkyl;
(10) 3- to 8-membered monocyclic non-aromatic heterocyclic group;
(11) 5- or 6-membered monocyclic aromatic heterocyclic group optionally substituted by 1 to 3 substituents selected from: (a) halogen atom, (b) cyano.

[3] The compound or salt thereof of the above [1], where $R_2$ is phenyl, or aromatic 5- to 6-membered heterocyclyl, where a ring is optionally substituted by one or more $R^1$ groups;

each $R^1$ is independently halogen, CN, C(O)OR$^2$, OR$^2$, C(O)R$^2$, S(O)$_2$R$^2$, S(O)R$^2$, NO$_2$, OC(O)R$^2$, $C_{1-6}$ alkyl, $C_{2-6}$ alkenyl or $C_{2-6}$ alkynyl, where the $C_{1-6}$ alkyl, $C_{2-6}$ alkenyl and $C_{2-6}$ alkynyl are optionally substituted by one or more $R^3$ groups which are identical or different;

$R^2$ is independently selected from H, $C_{1-6}$ alkyl, $C_{2-6}$ alkenyl or $C_{2-6}$ alkynyl, where the $C_{1-6}$ alkyl, $C_{2-6}$ alkenyl or $C_{2-6}$ alkynyl are optionally substituted by one or more $R^3$ groups which are identical or different;

$R^3$ is halogen, CN, C(O)OR$^4$, OR$^4$, C(O)R$^4$, S(O)$_2$R$^4$, S(O)R$^4$, NO$_2$, OC(O)R$^4$;

$R^4$ is independently selected from H, $C_{1-6}$ alkyl, $C_{2-6}$ alkenyl or $C_{2-6}$ alkynyl, where $C_{1-6}$ alkyl, $C_{2-6}$ alkenyl and $C_{2-6}$ alkynyl are optionally substituted by one or more halogens which are identical or different.

[4] The compound or the pharmaceutically acceptable salt thereof of any one of the above claims 1 to 3, where the compound is selected from:

N-(3-((6-aniline-1H-pyrazolo[3,4-d]pyrimidin-1-yl)methyl)phenyl)acrylamide;

N-(3-((6-aniline-1H-pyrazolo[3,4-d]pyrimidin-1-yl)methyl)phenyl)but-2-enamide; N-(3-((6-((4-morpholinylphenyl)amino)-1H-pyrazolo[3,4-d]pyrimidin-1-yl)methyl)phenyl)acrylamide;

N-(3-((6-((4-morpholinylphenyl)amino)-1H-pyrazolo[3,4-d]pyrimidin-1-yl)methyl)phenyl)but-2-enamide;

N-(3-((6-((4-(4-methylpiperazin-1-yl)phenyl)amino)-1H-pyrazolo[3,4-d]pyrimidin-1-yl)methyl)phenyl)acrylamide;

N-(3-((6-((4-(4-methylpiperazin-1-yl)phenyl)amino)-1H-pyrazolo[3,4-d]pyrimidin-1-yl)methyl)phenyl)but-2-enamide;

N-(3-((6-((1-(2-methoxy-ethyl)-1H-pyrazol-4-yl)amino)-1H-pyrazolo[3,4-d]pyrimidine-1-yl)methyl)phenyl)acrylamide;

N-(3-((6-((1-(2-methoxy-ethyl)-1H-pyrazol-4-yl)amino)-1H-pyrazolo[3,4-d]pyrimidine-1-yl)methyl)phenyl)but-2-enamide;

N-(3-((6-((1-(2-hydroxyethyl)-1H-pyrazol-4-yl)amino)-1H-pyrazolo[3,4-d]pyrimidin-1-yl)methyl)phenyl)acrylamide;

N-(3-((6-((1-(2-hydroxyethyl)-1H-pyrazol-4-yl)amino)-1H-pyrazolo[3,4-d]pyrimidin-1-yl)methyl)phenyl)but-2-enamide;

N-(4-((6-((1-(2-hydroxyethyl)-1H-pyrazol-4-yl)amino)-1H-pyrazolo[3,4-d]pyrimidin-1-yl)methyl)phenyl)acrylamide;

N-(4-((6-((4-morpholinylphenyl)amino)-1H-pyrazolo[3,4-d]pyrimidin-1-yl)methyl)phenyl)acrylamide;

N-(4-((6-((4-(4-methylpiperazin-1-yl)phenyl)amino)-1H-pyrazolo[3,4-d]pyrimidin-1-yl)methyl)phenyl)acrylamide.

[5] The medicament of claims 1-4, which is a JAK inhibitor.

[6] The medicament of claim 5, which is a medicament for preventing, treating and/or improving an autoimmune disease.

[7] The medicament of claim 6, where the autoimmune disease is psoriasis, rheumatoid arthritis, inflammatory bowel disease, Sjogren's syndrome, Behcet's disease, multiple sclerosis or systemic lupus erythematosus.

[8] Use of the compound or the salt thereof of claim 1 in the preparation of a medicament for preventing and/or improving an autoimmune disease.

[9] The use of claim 8, where the autoimmune disease is psoriasis, rheumatoid arthritis, inflammatory bowel disease, Sjogren's syndrome, Behcet's disease, multiple sclerosis or systemic lupus erythematosus.

Beneficial Effects of the Invention

The compound (I) has excellent JAK-3 inhibitory activity, and can be used as a medicament to prevent, treat and/or improve an autoimmune disease (e.g., psoriasis, rheumatoid arthritis, inflammatory bowel disease, Sjogren's syndrome, Behcet's disease, multiple sclerosis, systemic lupus erythematosus and the like).

DETAILED DESCRIPTION OF THE INVENTION

In this description, "halogen atom" refers to a fluorine atom, a chlorine atom, a bromine atom or an iodine atom.

In this description, "$C_{1-6}$ alkyl (group)" refers to $C_{1-6}$ alkyl, $C_{2-7}$ alkenyl, $C_{1-6}$ alkoxy, $C_{2-6}$ alkenoxy, $C_{1-6}$ alkyl-carbonyl mono- or di-substituted amidoaryl, or the like.

In this description, "$C_{1-6}$ alkyl (group)" refers to methyl, ethyl, isopropyl, butyl, sec-butyl, pentyl, isopentyl, 1-ethylpropyl, 1-methylbuthyl, isohesyl, 1,1-dimethylbutyl, 3,3-dimethylbutyl, 2-ethylbutyl, 1-ethyl-2-methylpropyl, 1,2-dimethylpropyl, or the like.

In this description, "$C_{2-7}$ alkenyl (group)" refers to vinyl, 1-propenyl, 2-methyl-1-propenyl, 1-butenyl, 2-butenyl, 3-butenyl, 3-methyl-2-butenyl, 1-pentenyl, 4-methyl-3-pentenyl, 3-hexenyl, 5-hexenyl, or the like.

In this description, "$C_{2-7}$ alkynyl (group)" refers to acetenyl, 1-propinyl, 2-propinyl, 3-butynyl, 1-pentynyl, 1,1-dimethylprop-2-alkyne-1-yl, 1-hexynyl, 2-hexynyl, 3-hexynyl, 4-hexyny, 5-hexynyl, or the like.

In this description, "$C_{1-6}$ alkoxy (group)" refers to methoxy, ethoxy, propoxy, isopropoxy, butoxy, isobutoxy, sec-butoxy, tert-butoxy, pentyloxy, isopentyloxy, neopentyloxy, hexyloxy, or the like.

In this description, "$C_{2-6}$ alkenoxy (group)" refers to ethylnenoxy, 1-ethenyloxy, 1-propenyloxy, 2-propenyloxy, 2-methyl-1-propenyloxy, 1-butenyloxy, 2-butenyloxy, 4-methyl-3-pentenyloxy, 1-hexenyloxy, 3-hexenyloxy, 5-hexenyloxy, or the like.

In this description, "$C_{1-6}$ alkyl-carbonyl mono- or di-substituted amidoaryl (group)" refers to N, N-dimethyl formyl, N, N-dimethyl acetyl, or the like.

In this description, "$C_{6-14}$ aryl (group)" refers to phenyl, 1-naphthyl, 2-naphthyl, or the like.

In this description, an example of "monocyclic aromatic heterocyclic group" includes a 5- to 7-membered (preferably, 5- or 6-membered) monocyclic aromatic heterocyclic group as a ring to constitute an atom; besides carbon atom, the group further includes 1 to 4 heteroatoms selected from oxygen atom, sulphur atom (optionally oxidized) and nitrogen atom (optionally oxidized), for example, furyl (e.g., 2-furyl, 3-furyl), thienyl (e.g., 2-thienyl, 3-thienyl), pyridyl (e.g., 2-pyridyl, 3-pyridyl, 4-pyridyl), pyrimidyl (e.g., 2-pyrimidyl, 4-pyrimidyl, 5-pyrimidyl), pyridazinyl (e.g., 3-pyridazinyl, 4-pyridazinyl), pyrazinyl (e.g., 2-pyrazinyl), pyrryl (e.g., 1-pyrryl, 2-pyrryl, 3-pyrryl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), or the like.

In this description, "non-aromatic heterocyclic group" refers to a monocyclic non-aromatic heterocyclic group and a polycyclic non-aromatic heterocyclic group.

In this description, an example of "monocyclic non-aromatic heterocyclic group" includes a 3- to 8-membered (preferably 5- or 6-membered) monocyclic non-aromatic heterocyclic group as a ring to constitute an atom; besides carbon atoms, the group further includes 1 to 4 heteroatoms selected from oxygen atoms, and sulphur atoms (optionally oxidized), for example, azacyclobutyl (e.g., 1-azacyclobutyl, 2-azacyclobutyl), pyrrolidyl (e.g., 1-pyrrolidyl, 2-pyrrolidyl), piperidyl (e.g., piperidino-(1-position only), 2-piperidyl, 3-piperidyl, 4-piperidyl), or the like.

In this description, an example of "polycyclic non-aromatic heterocyclic group" includes 8- to 22-membered polycyclic non-aromatic heterocyclic groups, and specifically, a group derived from a condensed ring, where a ring equivalent to the above 3- to 8-membered monocyclic non-aromatic heterocyclic group is condensed with a $C_{6-14}$ aromatic hydrocarbon; a group derived from a condensed ring, where a ring equivalent to the above 3- to 8-membered monocyclic non-aromatic heterocyclic group is a condensed ring; a group derived from a condensed ring, where a ring corresponding to the above 3- to 8-membered monocyclic non-aromatic heterocyclic group is condensed with a ring corresponding to the above 5- to 7-membered monocyclic non-aromatic heterocyclic group; and the above groups are partial saturated groups; such as, dihydroindolyl (e.g., 2,3-dihydro-1H-indol-1-yl), dihydroisoindolinyl (e.g., 1,3-dihydro-2H-isoindol-2-yl), dihydrobenzofuryl (e.g., 2,3-dihydro-1-benzfuran-5-yl), or the like.

When the compound (I) is a form of salt, an example thereof includes: metal salt, ammonium salt, salt formed with organic alkali, salt formed with inorganic acid, salt formed with organic acid, salt formed with alkaline or acidic amino acids, and the like. A preferable example of the metal salt includes: alkali metal salt, such as sodium salt, and kali salt; alkaline-earth metal salt, such as calcium salt, magnesium salt, barium salt; and the like. A preferable example of the salt formed with organic alkali includes salt formed with the following organic alkali: trimethylamine, triethylamine, pyridine, methylpyridine, 2,6-dimethyl pyridine, ethanol amine, diethanol amine, triethanolamine, cyclohexane, dicyclohexyl amine, N,N'-dibenzylethylenediamine, and the like. A preferable example of the salt formed with inorganic acids includes: salt formed with hydrochloric acid, hydrobromic acid, nitric acid, sulfuric acid, phosphoric acid, and the like. A preferable example of the salt formed with organic acids includes salt formed with the following organic acids: formic acid, acetic acid, trifluoroacetic acid, phthalic acid, fumaric acid, oxalic acid, tartaric acid, maleic acid, citric acid, succinic acid, malic acid, methylsulfonic acid, benzenesulfonic acid, p-toluenesulfonic acid, and the like. A preferable example of the salt formed with alkaline amino acids includes salt formed with arginine, lysine, ornithine, and the like. A preferable example of the salt formed with an acidic amino acid includes salts formed with aspartic acid, glutamic acid, and the like.

Preferably, pharmaceutical salt is taken among them. For example, when the compound has an acidic functional group, the example thereof includes inorganic salt, such as alkali metal salt (e.g., sodium salt, kali salt), alkaline-earth metal salt (e.g., calcium salt, magnesium salt), ammonium salt and the like; when the compound has an alkaline functional group, the example thereof includes salt formed with inorganic acids, such as, hydrochloric acid, hydrobromic acid, nitric acid, sulfuric acid, phosphoric acid; as well as salt formed with organic acids, such as, acetic acid, phthalic acid, fumaric acid, oxalic acid, tartaric acid, maleic acid, citric acid, succinic acid, methylsulfonic acid, benzenesulfonic acid, p-toluenesulfonic acid.

Preparation Method:

The preparation method for the compound (I) or salt thereof of the present disclosure will be specified below:

The compound (I) and the feedstock compounds can be prepared by a method known in the art, for example, a method as shown in the following reaction route, and the like. In each step of the following preparation method, "room temperature" usually refers to 5-40° C.; unless otherwise stated, each symbol in the chemical formula described in the reaction route above is as mentioned above. In compounds of the chemical formula, each compound includes salt, and an example of the salt includes salt similar to the salt of the compound (I), and the like.

In each reaction, when the feedstock compounds or intermediates have amino, carboxyl or hydroxyl as a substituent, generally, these groups can be protected by a protecting group used by a chemical peptide and the like. After the reaction, the protecting group is removed according to the requirements to obtain a target compound. Introduction and removal of the protecting group can be performed according to a method known in the art, for example, a method described in "Protective Groups in Organic Synthesis, 4th Ed", Wiley-Interscience, Inc. (2006) (Theodora W. Greene, Peter G. M. Wuts).

An example of an amino protecting group includes: formyl group, $C_{1-6}$-alkyl-carbonyl, $C_{1-6}$ alkoxy-carbonyl, benzoyl, $C_{7-10}$ aralkyl-carbonyl (e.g., benzylcarbonyl), $C_{7-12}$ aralkyloxy-carbonyl (e.g., carbobenzoxy, 9-fluorenylmethoxycarbonyl), trityl, phthaloyl, N,N-dimethylamino methylene, silyl optionally substituted by $C_{1-6}$ alkyl (e.g., trimethylsilyl, triethylsilyl, dimethylphenylsilyl, tert-butyldimethylsilyl, tert-butyldiethylsilyl), C$_{2-6}$ alkenyl (e.g., 1-propenyl), and the like. These groups are optionally substituted by 1 to 3 substituents selected from halogen atom, C$_{1-6}$ alkoxy and nitryl.

An example of a carboxyl protecting group includes: C$_{1-6}$ alkyl, C$_{7-12}$ aralkyl (e.g., benzyl), phenyl, trityl, silyl optionally substituted by C$_{1-6}$ alkyl (e.g., trimethylsilyl, triethylsilyl, dimethylphenylsilyl, tert-butyldimethylsilyl, tert-butyldiethylsilyl), C$_{2-6}$ alkenyl (e.g., 1-propenyl), and the like.

An example of a hydroxyl protecting group includes: C$_{1-6}$ alkyl, phenyl, trityl groups, C$_{7-12}$ aralkyl (e.g., benzyl), formyl, C$_{1-6}$ alkyl-carbonyl, benzoyl, C$_{7-12}$ aralkyloxy-carbonyl (e.g., benzylcarbonyl), 2-tetrahydropyranyl, 2-tetrahydrofurfuryl, silyl optionally substituted by C$_{1-6}$ alkyl (e.g., trimethylsilyl, triethylsilyl, dimethylphenylsilyl, tert-butyldimethylsilyl, tert-butyldiethylsilyl), C$_{2-6}$ alkenyl (e.g., 1-propenyl), and the like.

These groups are optionally substituted by 1 to 3 substituents selected from halogen atom, C$_{1-6}$ alkyl, C$_{1-6}$ alkoxy and nitryl.

These protecting groups can be removed by a method known in the art, for example, a method described in "Protective Groupsin Organic Synthesis, 4th Ed", Wiley-Interscience, Inc. (2006) (Theodora W. Greene, Peter G. M. Wuts), and the like. Specifically, a method of using acid, alkali, ultraviolet light, hydrazine, phenylhydrazine, sodium N-methyl dithiocarbamate, tetrabutylammonium fluoride, palladium acetate, trialkylsilyl halogen (e.g., trimethylsilyl iodide, trimethylsilyl bromine) and the like, may be used.

A microwave radiator may be used if necessary for the reaction in the synthetic procedure under microwave radiation.

The compound obtained in each step may be directly used in the next step as a reaction mixture or a crude product, or may be separated from a reaction mixture according to a conventional method, and may be readily purified by a separation method, such as, recrystallization, distillation and chromatography.

For example, the compound (I) can be prepared according to the following method A or a similar method thereof. Feedstock compounds in each method can be purchased commercially or prepared by a method known in the art or a similar method thereof.

In the compound (I), the compound represented by the Formula (I-A) is as follows:

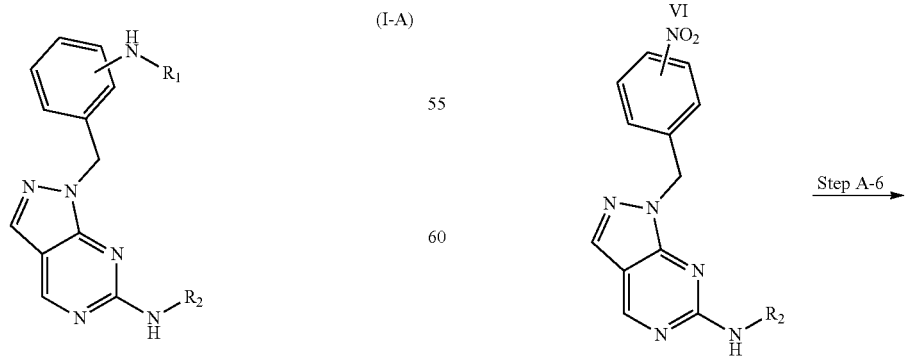

(I-A)

where, each symbol in the chemical formula is as mentioned above, (abbreviated as the compound (I-A) hereinafter); and the compound can be prepared by a method A below or a similar method thereof. In each step of the preparation method, feedstock compounds can be in a form of salt. An example of the salt includes those salts similar to the salt of compound (I).

Method A

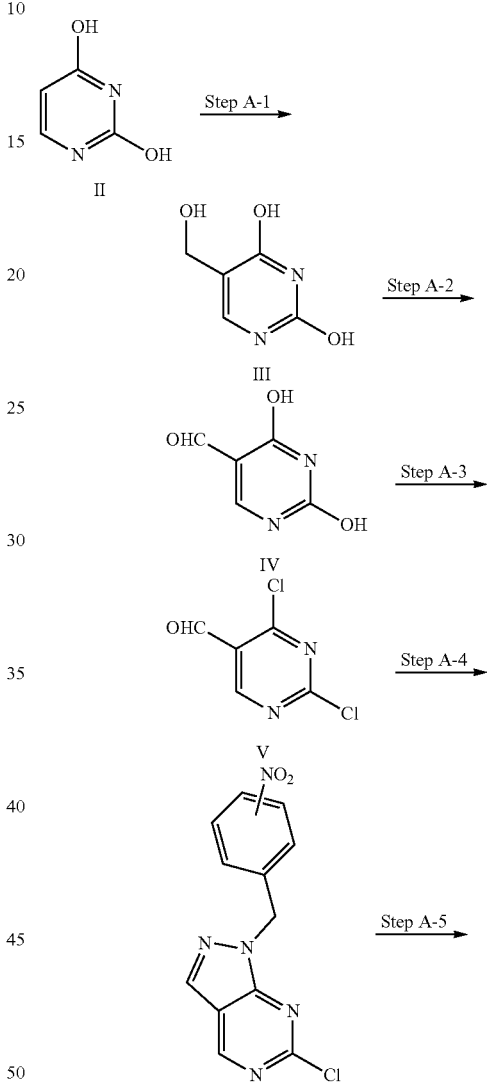

where, each symbol is as mentioned above.

In the method, a compound (II) as a starting material can be purchased commercially or prepared by a method known in the art or a similar method thereof.

Step A-1

The step refers to the reaction between the compound (II) and paraformaldehyde to transform the compound (II) into a compound (III).

In 1 mol compound (II), the use amount of paraformaldehyde and alkali is about 1 mol to about 100 mol, preferably, about 1 mol to about 10 mol.

An example of the alkali used includes: organic amines (such as, trimethylamine, triethylamine), alkali metal salts (such as, sodium bicarbonate), metal hydrides (such as, potassium hydride), alkali alcoholates (such as, sodium methylate), alkali metal disilylamides (such as, lithium disilylamide), and the like. Alkali metal salts (such as, sodium carbonate, potassium carbonate, and cesium carbonate) are taken preferably among them.

In the step, solvent is not limited specifically, and solvent may be or not be present as long as the reaction is available. An example thereof includes: hydrocarbons (such as, benzene, methylbenzene, xylene, hexane, heptane), halohydrocarbons (such as, chloroform, dichloromethane), ethers (such as, diethyl ether, diisopropyl ether, methyl tert-butyl ether), tetrahydrofuran, 1,4-dioxane, 1,2-dimethoxyethane), nitriles (such as, acetonitrile), aprotic polar solvents (such as, N,N-dimethylformamide, dimethylsulfoxide, hexamethylphosphoramide), aprotic polar solvents (such as, water, methyl alcohol, ethyl alcohol, 1-propyl alcohol, 2-propyl alcohol, 1-butanol, 2-methyl-2-propyl alcohol), and mixtures thereof.

In the step, the reaction temperature is usually about −50°C to about 200° C., preferably, about −10° C. to about 100° C. In the step, the reaction time is usually about 0.1 h to about 100 h.

The compound (III) obtained thereby can be separated and purified by a separation and purification method known in the art, such as, concentration, concentration under reduced pressure, solvent extraction, crystallization, recrystallization, phase transition, chromatography. Moreover, the compound (III) can be directly used in the next reaction without purification.

Step A-2

The step refers to the oxidation reaction subjected to the compound (III) to transform the compound (III) into a compound (IV).

In 1 mol compound (III), the use amount of an oxidant and a catalyst is about 1 mol to about 100 mol, preferably, about 1 mol to about 30 mol.

In the step, the oxidant is not limited specifically as long as the reaction is available. An example thereof includes: potassium persulfate, potassium permanganate, and the like.

In the step, the catalyst is not limited specifically, and the catalyst may be or not be present as long as the reaction is available. An example thereof includes: silver nitrate and the like.

In the step, solvent is not limited specifically, and solvent may be or not be present as long as the reaction is available. An example thereof includes: hydrocarbons (such as, benzene, methylbenzene, xylene, hexane, heptane), halohydrocarbons (such as, chloroform, dichloromethane), ethers (such as, diethyl ether, diisopropyl ether, methyl tertiary butyl ether), tetrahydrofuran, 1,4-dioxane, 1,2-dimethoxyethane), nitriles (such as, acetonitrile), aprotic polar solvents (such as, N,N-dimethylformamide, dimethylsulfoxide, hexamethylphosphoramide), aprotic polar solvents (such as, water, methyl alcohol, ethyl alcohol, 1-propyl alcohol, 2-propyl alcohol, 1-butanol, 2-methyl-2-propyl alcohol), and mixtures thereof.

In the step, the reaction temperature is usually about −50° C. to about 200° C., preferably, about 20° C. to about 100° C. In the step, the reaction time is usually about 0.1 h to about 100 h.

The compound (IV) obtained thereby can be separated and purified by a separation and purification method known in the art, such as, concentration, concentration under reduced pressure, solvent extraction, crystallization, recrystallization, phase transition, chromatography. Moreover, the compound (IV) can be directly used in the next reaction without purification.

Step A-3

The step refers to the halogenation reaction between the compound (IV) and a halogenated reagent to transform the compound (IV) into a compound (V).

In 1 mol compound (V), the use amount of the halogenated reagent is about 1 mol to about 100 mol, preferably, about 1 mol to about 10 mol.

An example of the halogenated reagent includes: fluorine, chlorine, bromine, iodine, NBS, NIS, and the like, and preferably, bromine and iodine.

In the step, solvent is not limited specifically as long as the reaction is available. An example thereof includes: hydrocarbons (such as, benzene, methylbenzene, xylene, hexane, heptane), halohydrocarbons (such as, chloroform, dichloromethane), ethers (such as, diethyl ether, diisopropyl ether, methyl tertiary butyl ether), tetrahydrofuran, 1,4-dioxane, 1,2-dimethoxyethane), nitriles (such as, acetonitrile), aprotic polar solvents (such as, N,N-dimethylformamide, dimethylsulfoxide, hexamethylphosphoramide), aprotic polar solvents (such as, water, methyl alcohol, ethyl alcohol, 1-propyl alcohol, 2-propyl alcohol, 1-butanol, 2-methyl-2-propyl alcohol), and mixtures thereof.

In the step, the reaction temperature is usually about −50° C. to about 200° C., preferably, about 0° C. to about 200° C. In the step, the reaction time is usually about 0.1 h to about 100 h.

In the step, the reaction gas is not limited specifically, and the reaction gas may be or not be present as long as the reaction is available. A shield gas includes: nitrogen, argon and the like.

The compound (V) obtained thereby can be separated and purified by a separation and purification method known in the art, such as, concentration, concentration under reduced pressure, solvent extraction, crystallization, recrystallization, phase transition, chromatography, alkali-solution and acid-isolation. Moreover, the compound (V) can be directly used in the next reaction without purification.

Step A-4

The step refers to the substitution reaction between the compound (V) and a substituted benzylhydrazine reagent to transform the compound (V) into a compound (VI).

In 1 mol compound (VI), the use amount of the substituted benzylhydrazine reagent is about 1 mol to about 100 mol, preferably, about 1 mol to about 10 mol.

An example of the alkali used includes: organic amines (such as, trimethylamine, triethylamine), alkali metal salts (such as, sodium bicarbonate), metal hydrides (such as, potassium hydride), alkali alcoholates (such as, sodium methylate), alkali metal disilylamines (such as, lithium disilylamine), and the like. Alkali metal salts (such as, sodium carbonate, potassium carbonate, and cesium carbonate) are taken preferably among them.

In the step, solvent is not limited specifically as long as the reaction is available. An example thereof includes: hydrocarbons (such as, benzene, methylbenzene, xylene, hexane, heptane), halohydrocarbons (such as, chloroform, dichloromethane), ethers (such as, diethyl ether, diisopropyl ether, methyl tertiary butyl ether), tetrahydrofuran, 1,4-dioxane, 1,2-dimethoxyethane), nitriles (such as, acetonitrile), aprotic polar solvents (such as, N,N-dimethylformamide, dimethylsulfoxide, hexamethylphosphoramide), aprotic polar solvents methyl-2-propyl alcohol), and mixtures thereof.

In the step, the reaction temperature is usually about −50° C. to about 250° C. In the step, the reaction time is usually about 0.1 h to about 100 h.

In the step, the reaction gas is not limited specifically, and the reaction gas may be or not be present as long as the reaction is available. A shield gas includes: nitrogen, argon and the like.

The compound (VI) obtained thereby can be separated and purified by a separation and purification method known in the art, such as, concentration, concentration under reduced pressure, solvent extraction, crystallization, recrystallization, phase transition, chromatography, alkali-solution and acid-isolation. Moreover, the compound (VI) can be directly used in the next reaction without purification.

Step A-5

The step refers to the substitution reaction between the compound (VI) and a substituted reagent to transform the compound (VI) into a compound (VII).

In 1 mol compound (VI), the use amount of the substituted reagent is about 1 mol to about 100 mol, preferably, about 1 mol to about 10 mol.

In the step, solvent is not limited specifically as long as the reaction is available. An example thereof includes: hydrocarbons (such as, benzene, methylbenzene, xylene, hexane, heptane), halohydrocarbons (such as, chloroform, dichloromethane), ethers (such as, diethyl ether, diisopropyl ether, methyl tertiary butyl ether), tetrahydrofuran, 1,4-dioxane, 1,2-dimethoxyethane), nitriles (such as, acetonitrile), aprotic polar solvents (such as, N,N-dimethylformamide, dimethylsulfoxide, hexamethylphosphoramide), aprotic polar solvents methyl-2-propyl alcohol), and mixtures thereof.

In the step, the reaction temperature is usually about −50° C. to about 250° C. In the step, the reaction time is usually about 0.1 h to about 100 h.

In the step, the reaction gas is not limited specifically, and the reaction gas may be or not be present as long as the reaction is available. A shield gas includes: nitrogen, argon and the like.

The compound (VII) obtained thereby can be separated and purified by a separation and purification method known in the art, such as, concentration, concentration under reduced pressure, solvent extraction, crystallization, recrystallization, phase transition, chromatography, alkali-solution and acid-isolation. Moreover, the compound (VII) can be directly used in the next reaction without purification.

Step A-6

The step refers to the reduction reaction subjected to the compound (VII) to transform the compound (VII) into a compound (VIII).

In 1 mol compound (VIII), the use amount of a reduction reagent or a catalyst is about 1 mol to about 100 mol, preferably, about 1 mol to about 10 mol.

In the step, solvent is not limited specifically as long as the reaction is available. An example thereof includes: hydrocarbons (such as, benzene, methylbenzene, xylene, hexane, heptane), halohydrocarbons (such as, chloroform, dichloromethane), ethers (such as, diethyl ether, diisopropyl ether, methyl tertiary butyl ether), tetrahydrofuran, 1,4-dioxane, 1,2-dimethoxyethane), nitriles (such as, acetonitrile), aprotic polar solvents (such as, N,N-dimethylformamide, dimethylsulfoxide, hexamethylphosphoramide), aprotic polar solvents methyl-2-propyl alcohol), and mixtures thereof.

An example of the catalyst used includes: Pd—C, iron powder, zinc powder, nickel, platinum, borane catalysts, lanthanides metal chlorides, and the like.

In the step, the reaction temperature is usually about −50° C. to about 250° C. In the step, the reaction time is usually about 0.1 h to about 100 h.

In the step, the reaction gas is not limited specifically, and the reaction gas may be or not be present as long as the reaction is available. A shield gas includes: nitrogen, argon and the like.

The compound (VIII) obtained thereby can be separated and purified by a separation and purification method known in the art, such as, concentration, concentration under reduced pressure, solvent extraction, crystallization, recrystallization, phase transition, chromatography, alkali-solution and acid-isolation. Moreover, the compound (VIII) can be directly used in the next reaction without purification.

Step A-7

The step refers to the reaction between the compound (III) and acyl chloride to transform the compound (III) into a compound (I-A).

In 1 mol compound (VIII), the use amount of acyl chloride is about 1 mol to about 100 mol, preferably, about 1 mol to about 30 mol.

An example of the acyl chloride used includes: acrylamide, butenamide, and the like, and preferably, acrylamide and butenamide.

In the step, alkali is not limited specifically; and alkali may be or not be present as long as the reaction is available. An example of the alkali used includes: organic amines (such as, trimethylamine, triethylamine), alkali metal salts (such as, sodium bicarbonate), metal hydrides (such as, potassium hydride), alkali alcoholates (such as, sodium methylate), alkali metal disilylamines (such as, lithium disilylamine), and the like. Alkali metal salts (such as, sodium carbonate, potassium carbonate, and cesium carbonate) are used preferably among them.

In the step, solvent is not limited specifically, and solvent may be or not be present as long as the reaction is available. An example thereof includes: hydrocarbons (such as, benzene, methylbenzene, xylene, hexane, heptane), halohydrocarbons (such as, chloroform, dichloromethane), ethers (such as, diethyl ether, diisopropyl ether, methyl tertiary butyl ether), tetrahydrofuran, 1,4-dioxane, 1,2-dimethoxyethane), nitriles (such as, acetonitrile), aprotic polar solvents (such as, N,N-dimethylformamide, dimethylsulfoxide, hexamethylphosphoramide), aprotic polar solvents (such as, water, methyl alcohol, ethyl alcohol, 1-propyl alcohol, 2-propyl alcohol, 1-butanol, 2-methyl-2-propyl alcohol), and mixtures thereof.

In the step, the reaction temperature is usually about −50° C. to about 250° C., preferably, about −10°C to about 250° C. In the step, the reaction time is usually about 0.1 h to about 100 h.

In the step, the reaction gas is not limited specifically, and the reaction gas may be or not be present as long as the reaction is available. A shield gas includes: nitrogen, argon and the like.

The compound (I-A) obtained thereby can be separated and purified by a separation and purification method known in the art, such as, concentration, concentration under reduced pressure, solvent extraction, crystallization, recrystallization, phase transition, chromatography.

When the compound (I) has an optical isomer, a stereisomer, zone isomer, or a rotamer, these isomers are also contained in a range of the compound (I); and separated to obtain a form of single products according to a synthesis method and a separation method (such as, concentration, solvent extraction, column chromatography, recrystallization) known in the art. For example, when the compound (I) has an optical isomer, and the optical isomer split by the compound is also contained in the range of the compound (I).

The optical isomer can be prepared by a method known in the art. Specifically, the optical isomer is obtained by synthesizing an intermediate via optical activity or by the optical resolution to the racemic final product according to a method known in the art.

Optical resolution may be a method known in the art, such as, a fractional recrystallization method, a chiral column method, and a diastereomer method.

1) Fractional Recrystallization Method

In this method, an optical-activity compound (such as, (+)-mandelic acid, (−)-mandelic acid, (+)-tartaric acid, (−)-tartaric acid, (+)-1-phenylethylamine, (−)-1-phenylethylamine, cinchonine, (−)-cinchonine, brucine) is subjected to form racemate salt; and the salt is separated by a tractional recrystallization method; and if necessary, a dissociative optical isomer is obtained by a neutralization step.

2) Chiral Column Method

In this method, a racemate or salt thereof is applied on a column for separating an optical isomer (a chiral column) for separation. For example, a mixture of optical isomers is applied on a chiral column under liquid chromatography, such as, CHIRA1 series (manufactured by Daice1 Chemical Industries, Ltd.); the mixture is expanded by using water alone, various buffer solutions (such as, phosphate buffers) and organic solvents (such as, ethyl alcohol, methyl alcohol, isopropyl alcohol, acetonitrile, trifluoroacetic acid, triethylamine) or a mixture thereof as an eluant to separate the optical isomers. For example, a chiral column is used for separation under gas chromatography.

3) Diastereomer Method

In this method, a racemic mixture is prepared into a mixture of diastereomers by the chemical reaction between the racemic mixture and an optical-activity reagent; and the mixture of diastereomers is transformed into a single substance by a typical separation method (such as, a fractional recrystallization method, a chromatographic method), and subjected to chemical treatment, e.g., hydrolysis to separate the portion of the optical-activity reagent, thus obtaining the optical isomers. For example, when the compound (I) contains hydroxyl or primary or secondary amino in molecules, the compound and an optical-activity organic acid (such as, MTPA[α-methoxy-α-(trifluoromethyl) phenylacetic acid], (−)-menthoxy acetic acid) are subjected to condensation reaction to respectively obtain a diastereomer of an ester compound or an amide compound. When the compound (I) contains carboxyl, the compound and an optical-activity amine or an optical-activity alcohol reagent are subjected to condensation reaction to respectively obtain a diastereomer of an amide compound or an ester compound. The separated diastereomer is transformed into an optical isomer of the original compound by acid hydrolysis or alkaline hydrolysis.

The compound (I) may be a crystal.

The crystal of the compound (I) can be prepared by a crystallization method known in the art.

An example of the crystallization method includes: a solution crystallization method, a steam crystallization method, a melt crystallization method, and the like.

The "solution crystallization method" is usually a method of transforming a unsaturated state into a saturated state; and the method changes factors related to solubility of a compound (such as, solvent compositions, pH value, temperature, ion strength, redox state) or changes the amount of solvents. A specific example thereof includes: a concentration method, a slow cooling method, a reaction method (such as, a diffusion method, an electrolytic method), a hydrothermal growth method, a molten-salt growth method, and the like. An example of the solvent used includes: aromatic hydrocarbons (such as, methylbenzene, xylene), halohydrocarbons (such as, dichloromethane, chloroform), saturated hydrocarbons (such as, hexane, cyclohexane), ethers (such as, diethyl ether, diisopropyl ether, tetrahydrofuran), nitriles (such as, acetonitrile), ketones (such as, acetone), sulfoxides (such as, dimethylsulfoxide), amides (such as, N,N-dimethylformamide), esters (such as, methyl acetate, ethyl acetate), alcohols (such as, methyl alcohol, ethyl alcohol, isopropyl alcohol), water, and the like. These solvents may be used alone, or two or more solvents are combined in a proper proportion (e.g., 1:1 to 1:100 (a volume ratio)). A seed crystal may be used if necessary.

The "steam crystallization method" refers to a vaporization method (e.g., a sealed tube method, an airflow method), a gas-phase reaction method, a chemical migration method, and the like.

The "melt crystallization method" refers to normal condensation methods (such as, a single crystal control method, a temperature gradient method, a bridgman method), zone melting methods (a zone balance method, a floating zone method), specific growth methods (a V1S method, a liquid phase epitaxy method), and the like.

A preferred example of the crystallization method is as follows: the compound (1) is dissolved in a proper solvent (such as, alcohols, e.g., ethyl alcohol, isopropyl alcohol) at −20° C. to 120° ° C., and a solution obtained is cooled to a temperature lower than a dissolving temperature (such as, −10° ° C. to 50° ° C., preferably, −10° C. to 20° C.).

A crystal of the present disclosure obtained thereby can be separated, for example, filtration and the like.

The crystal obtained is usually analyzed by a crystal analysis method of X-ray powder diffraction. A mechanical method or an optical method, or the like can be used as a method for measuring crystal orientation.

The crystal of the compound (I) obtained by the above preparation method (hereinafter abbreviated as "the crystal of the present disclosure") has high purity, high quality, and high stability, and is even free from denaturation after being stored at general conditions for a long time. Moreover, the crystal of the present disclosure has superiority in biological characteristics (such as, pharmacodynamics (absorption, distribution, metabolism, discharge), effect expression), especially in the use of a medicament.

In the description, specific rotation ([α]D) refers to a value of specific rotation measured by a polarimeter.

In the description, melting point refers to, for example, a value of melting point measured by a micro-melting point measuring device, a differential scanning calorimetry (DSC) device, and the like.

A compound (I) in a form of a prodrug can be used. The prodrug of the compound (I) refers to a compound which can be transformed into the compound (I) due to the reaction caused by an enzyme, gastric acid and the like under physiological conditions in vivo, that is, a compound transformed into the compound (I) due to oxidation, reduction, hydrolysis reaction, and the like caused by an enzyme; a compound transformed into the compound (I) by hydrolysis reaction and the like (caused by gastric acid), and the like.

An example of the prodrug of the compound (I) includes:
(1) compounds obtained by the acylation, alkylation and phosphorylation on the amino of the compound (I) (for example, compounds obtained by performing the eicosacylation, alanylation, amylamido carbonylation, (5-methyl-2-oxo-1,3-dioxole-4-yl) methoxy carbonylation, tetrahydrofuranylation, pyrrolidyl methylation, neo-pentylacyloxy methylation, tert-butylation, ethoxy carbonylation, tert-butoxycarbonylation, acetylation or cyclopropyl carbonylation, or the like on the amino of the compound (I));
(2) compounds obtained by the acylation, alkylation, phosphorylation or boronation on the hydroxy of the compound (I) (for example, compounds obtained by performing the acetylation, palmitoylation, propionylation, pivalylation, succinylation, fumaroylation, alanylation, or dimethylaminomethyl carbonylation, or the like on the hydroxy of the compound (I));
(3) compounds obtained by the esterification or amidation on the carboxyl of the compound (I) (for example, compounds obtained by performing ethyl esterification, phenyl esterification, carboxymethyl esterification, dimethylamino methyl esterification, neo-pentylacyloxy methyl esterification, (5-methyl-2-oxo-1,3-dioxole-4-yl) methyl esterification, cyclohexyloxycarbonylethyl esterification or formamidation, or the like on the carboxyl of the compound (I), and the like. These compounds can be prepared by a method known in the art or by the compound (I).

The prodrug of the compound (I) also can be a compound capable of being transformed into the compound (I) under physiological conditions, as mentioned in the document below: "IYAKUHIN no KAIHATSU (Development of Pharmaceuticals)", Vo1. 7, Design of Molecules, p 163-198, Published by HIROKAWA SHOTEN (1990).

In the description, the prodrugs of the compound (I) and compound (II) are together abbreviated as the "compound of the present disclosure" at times.

The compound (I) may be a hydrate, non-hydrate, solvate or a non-solvate.

The compound (I) also includes a compound labeled by an isotope (such as, $^3H$, $^{14}C$, $^{35}S$, $^{125}I$).

The compound (I) further includes a deuterated form, where H is transformed into $^2H(D)$.

The compound (I) also includes tautomers thereof.

The compound (I) may be a pharmaceutical eutectic or salt thereof. The eutectic or salt thereof refers to a crystalline material consisting of two or more specific solids at room temperature, each of the solids has different physical properties (such as, structure, melting point, melting heat, hygroscopicity, solubility, and stability). The eutectic or salt thereof may be prepared by a cocrystallization method known in the art.

The compound (I) may be also used as a PET tracer agent.

Since the compound of the present disclosure has excellent JAK inhibitory activity, and based on the activity, the compound of the present disclosure also can be used as a safe medicament.

For example, the medicament of the present disclosure containing the compound of the present disclosure can be used as a medicament for preventing or treating JAK-related diseases of mammal (such as, mice, rat, hamster, rabbit, cat, dog, cattle, sheep, monkey, and human); more specifically, the diseases described in the following (1)-(4) (especially (2)).
(1) Inflammatory diseases (such as, acute pancreatitis, chronic pancreatitis, asthma, adult respiratory distress syndrome, chronic obstructive pulmonary disease (COPD), inflammatory bone diseases, inflammatory pulmonary diseases, inflammatory bowel diseases, celiac sprue, hepatitis, system inflammatory reaction syndrome (SIRS), post-operation or post-traumatic inflammation, pneumonia, nephritis, meningitis, urocystitis, sphagitis, gastric mucosal damage, meningitis, pelvospondylitis, arthritis, dermatitis, chronic pneumonia, bronchitis, pnlmonary infarction, silicosis, pulmonary nodule).
(2) Autoimmune diseases (such as, psoriasis, rheumatoid arthritis, inflammatory bowel diseases (e.g., Crohn's disease, ulcerative colitis), Sjogren's syndrome, Behcet's disease, multiple sclerosis, systemic lupus erythematosus, ankylosing spondylitis, polymyositis, dermatomyositis (DM), periarteritis nodosa (PN), mixed connected tissue (MCTD), scleroderma, lupus erythematosus *profundus*, chronic thyroiditis, Graves' disease, autoimmune gastritis, type I and type-II diabetes, autoimmune hemolytic anemia, autoimmune neutrocytopenia, thrombocytopenia, atopic dermatitis, chronic active hepatitis, myasthenia gravis, graft versus host disease, Addison's disease, abnormal immune response, arthritis, dermatitis, radiodermatitis) (especially, psoriasis, rheumatoid arthritis, inflammatory bowel diseases, Sjogren's syndrome, Behcet's disease, multiple sclerosis and systemic lupus erythematosus).
(3) Bone and joint degencrative diseases (such as, rheumatoid arthritis, osteoporosis, osteoarthritis).
(4) Phymatosis (such as, malignant tumor, neovascular glaucoma, infantile hemangioma, multiple myeloma, acute myeloblastic leukemia, chronic sarcoma, multiple myeloma, chronic myelocytic leukemia, metastatic pathological melanoma, Kaposi's sarcoma, proliferation of blood vessel, cachexia, metastatic lesions of breast cancers, lung cancers (such as, non-small cell lung cancer, small cell lung cancer, malignant mesothelioma), mesothelioma, pancreatic cancers (e.g., pancreiatic duct), stomach cancers (such as, mucinous adenocarcinoma, adenosquamous carcinoma), papillary adenocarcinoma, breast cancers (such as, invasive ductal carcinoma, ductal carcinoma in situ, inflammatory breast cancer), ovarian cancers (such as, ovarian epithelial cancer, extragonadal germ cell tumor, ovarian germ cell tumor, ovarian low malignant potential tumor), prostatic cancers (such as, androgen dependent prostate cancer, hormone refractory prostate cancer), liver cancers (such as, primary liver cancer, cholangiocarcinoma), thyroid cancers (e.g., medullary thyroid carcinoma), kidney cancers (such as, renal cell cancer, transitional cell carcinoma of kidney and ureter), metrocarcinoma, brain tumors (such as, epiphysis astrocytoma, pilocytic astrocytoma, diffuse astrocytoma, anaplastic astrocytoma), melanoma, sarcoma, bladder cancer, leukemia, including multiple myeloma, pituitary adenoma, glioma, acoustic neuroma, retinoblastoma, nasopharyngeal carcinoma, laryngocarcinoma, tongue cancer, thymoma, esophagus cancer, duodenal cancer, colorectal cancer, rectal cancer, liver cancer, pancreatic endocrine tumor, carcinoma of biliary duct, gallbladder carcinoma, carcinoma of penis, pelvic ureteral cancer, testiculoma, carcinoma of vulva, cervical cancer, endometrial cancer, sarcoma of uterus, chorionic diseases, vaginal cancer, skin cancer, mycosis/nosomycosis, basal cell carcinoma, soft tissue sarcoma, malignant lymphoma, Hodgkin's disease, myelodysplasia syndromes, acute lymphocytic leukemia, chronic lymphocytic leukemia, adult t-cell leukaemia, chronic myeloproliferative disorders, Kaposi's sarcoma, Castleman's disease, lymphoma, leukemia multiple myeloma, polycythemia vera, primary thrombocytosis, idiopathic myelofibrosis, chronic myelocytic leukemia, chronic monocytic leukemia, oxyphile leukocytosis syndromes, idiopathic myelofibrosis, systemic mastocytosis, pancreatic endocrine tumor, fibrous histiocytoma, leiomyosarcoma, rhabdomyosarcoma, and unknown primary carcinoma).

Preferably, the medicament of the present disclosure can be used as a medicament for preventing, treating and/or autoimmune diseases (such as, psoriasis, rheumatoid arthritis, inflammatory bowel diseases, Sjogren's syndrome, Behcet's disease, multiple sclerosis, systemic lupus erythematosus), inflammatory diseases, bone and joint degencrative diseases, or phymatosis, especially preferably, psoriasis, rheumatoid arthritis, inflammatory bowel diseases (preferably, Crohn's disease or ulcerative colitis), Sjogren's syndrome, Behcet's disease, multiple sclerosis, systemic lupus erythematosus, lymphoma, leukemia multiple myeloma, polycythemia vera, primary thrombocytosis, idiopathic myelofibrosis, chronic myelocytic leukemia, chronic monocytic leukemia, oxyphile leukocytosis syndromes, idiopathic myelofibrosis, and systemic mastocytosis.

In this text, the above "preventing" diseases refers that for example, a patient is administered the medicament of the present disclosure; and the patient is a patient who is at a high-risk state of attack due to some disease-associated factors, but the disease is not formed, or a patient where the disease has been formed, but there is no subjective symptom, or a patient who is afraid of the resurgence of a disease after receiving treatment.

The medicament of the present disclosure shows excellent pharmacodynamics (e.g., a half-life period of the medicament in plasma), low toxicity (such as, HERG inhibition, CYP inhibition, CYP induction), low drug interactions. The compound of the present disclosure can be directly used as a medicament, or prepared into a pharmaceutical composition as a medicament of the present disclosure by mixing with a pharmaceutical carrier according to a method known in the art or a preparation method of a conventional pharmaceutical formulation. The medicament of the present disclosure can be taken orally or parenterally administered to a mammal safely (such as, human, monkey, cattle, horse, pig, mice, rat, hamster, rabbit, cat, dog, sheep and goat).

The medicament containing the compound of the present disclosure can be safely administered separately, or administered by mixing with a pharmacologically acceptable carrier according to a method known in the art as a preparation method of a pharmaceutical formulation and through the following dosage forms: for example, tablets (including sugar coated tablets, film-coated tablets, sublingual tablets, orally disintegrating tablets, oral tablets, and the like), pills, powders, granules, capsules (including soft capsules, microcapsules), troches, syrups, solutions, emulsions, suspensions, controlled release formulations (such as, instantaneous release formulations, sustained release formulations, sustained-release microcapsules), aerosols, film agents (such as, oral disintegrating film agent, mouth mucosa-adhesive film agent), injections (such as, subcutaneous injection, intravenous injection, intramuscular injection, intraperitoneal injection), venous transfusion, transdermal absorption formulations, creams, ointments, lotions, adhesives, suppositories (such as, rectal suppository, vaginal suppository), pilules, nasal formulations, pulmonary formulations (inhalants), eye drops, and the like; moreover, the medicament can be taken orally or administered parenterally (such as, intravenously, intramuscularly, subcutaneously, by organs, intranasally, by drops, intracerebrally, intrarectally, endovaginally, intraperitoneally, by introtumor to the nearby of the tumor, and directly administered to a lesion).

The content of the compound of the present disclosure in the medicament of the present disclosure is about 0.01 wt % to about 100 wt % of the whole medicament. The dose is changed according to the administering patient, administration route, diseases and the like. For example, a patient (weight: about 60 kg) suffering from psoriasis, rheumatoid arthritis, inflammatory bowel disease, Sjogren's syndrome, Behcet's disease, multiple sclerosis or systemic lupus erythematosus is orally administered one to several parts of 0.1 mg/kg (weight) to about 500 mg/kg (weight) active ingredients (compound (I) per day, preferably, about 0.1 mg/kg (weight) to about 50 mg/kg (weight), and more preferably, about 0.1 mg/kg (weight) to about 30 mg/kg (weight).

In respect to a pharmaceutical carrier for preparing the medicament of the present disclosure, various kinds of organic or inorganic carrier substances traditionally used as formulations can be enumerated; for solid formulations, such as, excipients, lubricants, binders and disintegrants; or for liquid medicaments, such as, solvents, solubilizers, suspensions, isotonic agents, buffer agents, soothing agents. In addition, it is practical to use a proper amount of common additives, such as, preservatives, antioxidants, colorants, sweetening agents, adsorbents, wetting agents according to the conditions if necessary.

An example of the excipient includes: lactose, white sugar, D-mannitol, starch, corn starch, crystalline cellulose, and light anhydrous silicic acid, and the like.

An example of the lubricant includes: magnesium stearate, calcium stearate, talcum powder, colloidal silicon dioxide, and the like.

An example of the binder includes: microcrystalline cellulose, white sugar, D-mannitol, dextrin, hydroxypropyl cellulose, hydroxypropyl methyl cellulose, polyvinylpyrrolidone, starch, sucrose, gel, methylcellulose, sodium carboxymethylcellulose, and the like.

An example of the disintegrating agent includes: starch, carboxymethylcellulose, carboxymethylcellulose calcium, carboxymethyl starch sodium, 1-hydroxypropyl cellulose, and the like.

An example of the solvent includes: water for injection, alcohol, propylene glycol, polyethylene glycol, sesame oil, corn oil, olive oil, and the like.

An example of the solubilizer includes: polyethylene glycol, propylene glycol, D-mannitol, benzyl benzoate, ethyl alcohol, triaminomethane, cholesterol, triethanolamine, sodium carbonate, sodium citrate, and the like.

An example of the suspension includes: surfactants, such as, stearoyl triethanolamine, dodecyl sodium sulfate, lauryl alanine, lecithin, benzalkonium chloride, benzethonium chloride, glycerin monostearate; hydrophilic polymers, such as, polyvinyl alcohol, polyvinylpyrrolidone, sodium carboxymethylcellulose, methylcellulose, hydroxymethyl cellulose, hydroxyethyl cellulose, hydroxypropyl cellulose.

An example of the isotonic agent includes: glucose, sorbitol, sodium chloride, glycerin, D-mannitol, and the like.

An example of the buffer agent includes: buffer solutions, such as, phosphates, acetates, carbonates, and citrates.

An example of the soothing agent includes: phenylcarbinol and the like.

An example of the preservative includes: p-hydroxy benzoate, chlorbutanol, phenylcarbinol, phenethyl alcohol, dehydroacetic acid, sorbic acid, and the like.

An example of the antioxidant includes: sulfites, ascorbic acid, α-tocopherol, and the like.

To prevent or treat various kinds of diseases, the compound of the present disclosure can be used together with other medicaments. Hereafter, a medicament used together with the compound of the present disclosure is called "a combined medicament of the present disclosure".

For example, the compound of the present disclosure can be combined with the following drugs when used as a JAK-1 and/or JAK-3 inhibitor.

(1) Non-steroidal anti-inflammatory drugs (NSAID): including ① traditional NSAIDs; ② cyclo-oxygenase inhibitors (COX-1 selective inhibitor, COX-2 selective inhibitor, and the like); ③ NO-release NSAID; ④ JAK inhibitors, and the like;

(2) disease-modifying antirheumatic drugs (DMARD) for improving diseases:
① penicillamine; ② aminosalicylic acid drugs; ③ pyrimidine-synthesized inhibitors, and the like;

Besides the mentioned above, other combined drugs further include: antibacterial agents, antifungal agents, antiprotozoal drugs, antibiotics, antibechics and expectorants, sedatives, anesthetics, anti-ulcer drugs, antiarrhythmic drugs, antihypertensive/diuretic drugs, anticoagulants, tranquilizers, antipsychotic drugs, antitumor drugs, drugs to promote he decrease of serum lipids, muscle relaxants, antiepileptic drugs, antidepressants, antiallergic agents, cardiants, therapeutics of arrhythmia, vasodilator substances, angiotonics, therapeutics of diabetes, antinarcotics, vitamins, vitamin derivatives, antiasthmatics, therapeutic agents of pollakiuria/uracratia, antipruritics, therapeutic agents of atopic dermatitis, therapeutic agents of allergic rhinitis, hypertensors, endotoxin-antagonists or -antibodies, signal transduction inhibitors, inhibitors of inflammatory medium activity, antibodies inhibiting inflammatory medium activity, inhibitors of anti-inflammatory medium activity, antibodies inhibiting anti-inflammatory medium activity, and the like.

With regard to the combined use, the administration time of the compound of the present disclosure and the combined drug are not limited, and the compound of the present disclosure and the combined drug can be administered to a patient at the same time, or administered to a patient at different times. A dose of the "combined drug" can be determined according to a clinical dose; and can be selected properly according to the administering patient, administration route, diseases, combined drug, and the like.

An administering mode of the combined use is not limited specifically as long as the compound of the present disclosure can be combined with the combined drug. An example of the administering mode is as follows:

(1) administration of a single formulation obtained by processing the compound of the present disclosure and a combined drug at the same time; (2) simultaneous administration of two formulations of the compound of the present disclosure and a combined drug prepared respectively by the same administration route; (3) alternative administration of two formulations of the compound of the present disclosure and a combined drug prepared respectively by the same administration route; (4) simultaneous administration of two formulations of the compound of the present disclosure and a combined drug prepared respectively by different administration routes; (5) alternative administration of two formulations of the compound of the present disclosure and a combined drug prepared respectively by different administration routes (for example, administration according an order of the compound of the present disclosure and a combined drug, or administration according a reverse order), and the like.

In the combined medicament of the present disclosure, a mixing ratio of the compound of the present disclosure to the combined drug can be selected according to the administering patient, administration route, the disease and the like.

For example, even though the content of the compound of the present disclosure in the combined medicament of the present disclosure varies from the forms of the formulation, generally, it is about 0.01-100 wt % of the whole formulation, preferably, about 0.1-50 wt %, and more preferably, about 0.5-20 wt %.

In the combined medicament of the present disclosure, the content of the combined drug varies from the forms of the formulation, generally, it is about 0.01-100 wt % of the whole formulation, preferably, about 0.1-50% wt %.

Meanwhile, the content of the additive (e.g., a carrier) in the combined medicament of the present disclosure varies from the forms of the formulation, based on the formulation, it is generally about 1-99.99 wt %, preferably, about 10-90 wt %.

The same content is used when the compound of the present disclosure and the combined drug are prepared separately. The dose of the combined medicament varies from the type of the compound of the present disclosure, administration route, symptoms, age of the patient, and the like. For example, for an orally-administered patient (weight: about 60 kg) suffering from rheumatoid arthritis, the dose of the compound (I) is about 0.1 mg/kg (weight) to about 30 mg/kg (weight), preferably, about 1 mg/kg (weight) to about 20 mg/kg (weight), and the patient can be administered for once or several times per day.

Any amount of combined drug can be used as long as the side effect causes no problem. When the combined medicament of the present disclosure is administered, the compound of the present disclosure and the combined drug can be administered at the same time, or alternatively available. When a patient is administered at certain intervals, the interval time may vary from the active ingredients, dosage form and administration method; for example, when a combined drug is administered first, the following administration method is an example: after administering the combined drug, the compound of the present disclosure is administered within a time range from 1 min to 3 d, preferably, 10 min to 1 d, and more preferably, 15 min to 1 h. When the compound of the present disclosure is administered first, the following administration method is another example: after administering the compound of the present disclosure, a combined drug is administered within a time range from 1 min to 1 d, preferably, 10 min to 6 h, and more preferably, 15 min to 1 h.

EXAMPLES

The present disclosure will be explained more detailed with reference to reference examples, examples, experiment examples, and formulation examples hereinafter; these examples are not to be used to limit the present disclosure, and can be changed within the scope of the present disclosure.

In the examples below, "room temperature" generally refers to about 10° C. to about 35° C. A ratio represented by a mixed solvent is a mixing volume ratio, unless otherwise specified. Unless otherwise specified, % refers to wt %.

Alkaline silica gel refers to a silica gel bonded through aminopropylsilane in silica gel column chromatography. C18 refers to a silica gel bonded through octadecyl in high performance liquid chromatography (HPLC). A ratio of an elution solvent is a mixing volume ratio, unless otherwise specified.

The following abbreviations are used in the examples and experiment examples below.

THF: tetrahydrofuran,
DIEA: N,N-diisopropylethylamine
M: molar concentration.
$^1$H-NMR (proton magnetic resonance spectrum) is measured by using Fourier-transformation NMR. ACD/SpecManager, and the like are used for analysis. A peak of a very light proton (such as, hydroxyl, amino) is not described herein.

MS (mass spectrum) is measured by 1C/MS (Liquid Chromatography-Mass Spectrometery). As an ionization method, ESI (electrospray ionization) method and the like are used. Data shows those measured values. Usually, molecular ion peaks are observed. A dissociative molecular ion peak or fragment ion peak is observed usually under a condition of salt.

Reference Example 1

3-Nitrylbenzylhydrazine hydrochloride

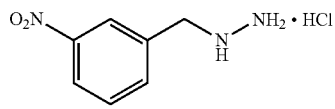

85% hydrazine hydrate (62 g) dissolved by 160 mL ethyl alcohol were added to a 500 ml three-necked flask, heated for reflux, and 3-nitrobenzyl chloride (20 g) dissolved by 72 mL ethyl alcohol was dropwisely added to the flask, and stirred for reaction for 3 h at a reflux temperature, where the adding time was about 1 h. The reaction was monitored by a spot plate. At the end of the reaction, the flask was cooled to room temperature, and dried under reduced pressure; and residuals were dissolved by 300 mL EA. 100 ml saturated salt solution was added for washing twice, and the aqueous layer was extracted by 200 mL EA, organic phases were combined, and dried by adding anhydrous Na$_2$SO$_4$, and rotary dried under reduced pressure; then 150 mL EA was added to dissolve residuals, and a HCl methanol solution was added to a solution to salify and separate out a product, and the product was subjected to suction filtration to obtain a white to faint yellow powder.

MS(ESI$^+$): [M+H]$^+$ 168.1.

Reference Example 2

4-Nitrylbenzylhydrazine hydrochloride

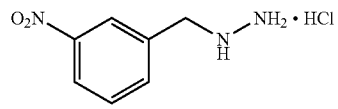

The title compound was obtained by 4-nitrylbenzyl chloride and hydrazine hydrate with reference to the method the same as that in reference example 1.

MS(ESI$^+$): [M+H]$^+$ 168.1.

Reference Example 3

1-(2-methoxyethyl)-4-nitryl-1H-pyrazol

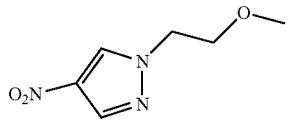

4-Nitropyrazole (5 g), K$_2$CO$_3$ (9.17 g), 2-bromo-ethylmethyl ether (7.38 g), KI (1.47 g) and 63 mL CH$_3$CN were added to a 100 mL eggplant-shaped flask for reflux overnight. At the end of the reaction, the flask was rotary dried under reduced pressure; 75 ml H$_2$O and 50 mL×3 EA were added, and an organic layers were combined, and washed by a saturated salt solution; and organic phases were added by adding anhydrous Na$_2$SO$_4$ and dried under reduced pressure to obtain an oily product.

MS(ESI$^+$): [M+H]$^+$ 172.2.

Reference Example 4

1-Methyl-4-nitryl-1H-pyrazol

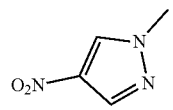

The title compound was obtained by 4-nitropyrazole and iodomethane with reference to the method the same as that in reference example 3.

MS(ESI$^+$): [M+H]$^+$ 128.2.

Reference Example 5

2-(4-Nitryl-1H-pyrazol-1-yl)ethyl alcohol

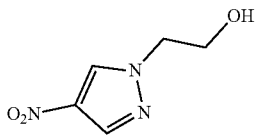

The title compound was obtained by 4-nitropyrazole, KI and 2-bromoethanol with reference to the method the same as that in reference example 3.

MS(ESI$^+$): [M+H]$^+$ 158.2.

Reference Example 6

4-(4-Nitrophenyl)morpholine

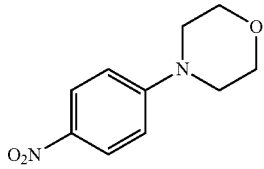

4-Fluoronitrobenzene (1 g), K$_2$CO$_3$ (1.08 g) and 6 mL DMSO were added to a single-necked flask, and stirred at room temperature for reaction for 30 min, and morpholine (0.62 g) was added dropwisely for reaction for 2 h after heating up to 120° C., and the reaction was monitored by a spot plate. A mixture was poured to a mixed liquor of alcohol and water (1:1), and yellow precipitates were filtered to obtain a product.

MS(ESI$^+$): [M+H]$^+$ 209.2.

Reference Example 7

1-Methyl-4-(4-nitrophenyl)piperidine

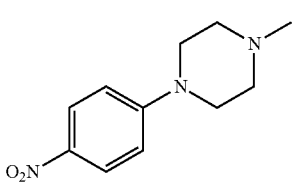 [SMILES: CN1CCN(c2ccc([N+](=O)[O-])cc2)CC1]

The title compound was obtained by 4-fluoronitrobenzene and N-methylpiperidine with reference to the method the same as that in reference example 6.

MS(ESI$^+$): [M+H]$^+$ 222.2.

Reference Example 8

1-(2-Methoxyethyl)-1H-pyrazol-4-amino

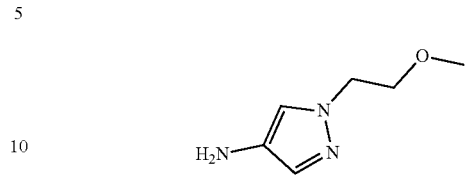

1-(2-methoxyethyl)-4-nitryl-1H-pyrazol (5 g), Pd/C (1 g) and 50 mL ethyl alcohol were added to a single-necked flask for reaction for about 24 h at room temperature after air was replaced by a hydrogen balloon. At the end of the reaction, suction filtration under reduced pressure was performed by diatomite, and drying under reduced pressure was performed to obtain a product.

MS(ESI$^+$): [M+H]$^+$ 142.2.

Reference Example 9

1-Methyl-1H-pyrazol-4-amino

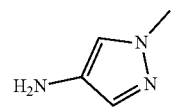

The title compound was obtained by 1-methyl-4-nitryl-1H-pyrazol and Pd/C with reference to the method the same as that in reference example 8.

MS(ESI$^+$): [M+H]$^+$ 98.1.

Reference Example 10

2-(4-Amino-1H-pyrazol-1-yl)ethyl alcohol

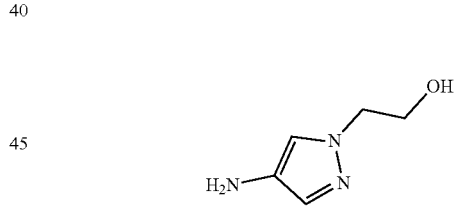

The title compound was obtained by 1-methyl-4-nitryl-1H-pyrazol and Pd/C with reference to the method the same as that in reference example 8.

MS(ESI$^+$): [M+H]$^+$ 128.2.

Reference Example 11

4-Morpholinoaniline

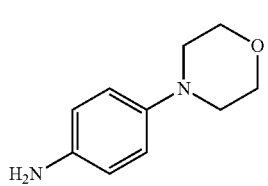

The title compound was obtained by 4-(4-nitrophenyl) and Pd/C with reference to the method the same as that in reference example 8.

MS(ESI$^+$): [M+H]$^+$ 179.2.

Reference Example 12

4-(4-Methylpiperazin-1-yl)aniline

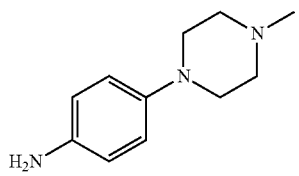

The title compound was obtained by 1-methyl-4-(4-nitrophenyl)piperidine and Pd/C with reference to the method the same as that in reference example 8.

MS(ESI$^+$): [M+H]$^+$ 192.2.

Example 1

N-(3-((6-((1-(2-methoxyethyl)-1H-pyrazol-4-yl)amino)-1H-pyrazolo[3,4-d]pyrimidine-1-yl)methyl)phenyl)acrylamide

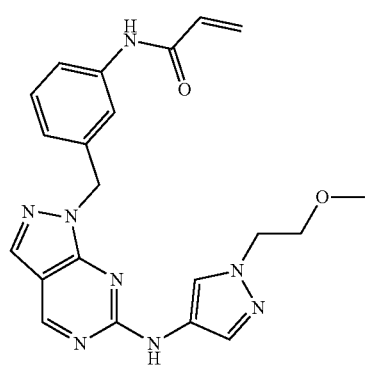 [SMILES: C=CC(=O)Nc1cccc(Cn2ncc3cnc(Nc4cnn(CCOC)c4)nc32)c1]

A) 6-chloro-1-(3-nitrobenzyl)-1H-pyrazolo[3,4-d]pyrimidine 4,6-Dichloro-pyrimidine-5-formaldehyde (8.4 g) and 240 mL THF were added to a 500 ml three-necked flask, and Net3$_3$ (14.56 g) was added at 0° C., where the temperature was not greater than 0° C., and stirred for 10 min after dropwise adding, then, 3-nitrylbenzylhydrazine hydrochloride (9.74 g) was added slowly, where the temperature was controlled within 0°C during adding process, and stirred for reaction for 1-2 h after feeding; at the end of the reaction, drying under reduced pressure was performed to obtain a crude product, and the crude product was stirred, separated and purified by silica gel column chromatography to obtain a title compound.

MS(ESI$^+$): [M+H]$^+$ 290.2.

B) N-(1-(2-methoxyethyl)-1H-pyrazol-4-yl)-1-(3-nitrobenzyl)-1H-pyrazolo[3,4-d]pyrimidine-6-amino 6-chloro-1-(3-nitrobenzyl)-1H-pyrazolo[3,4-d]pyrimidine (0.1 g), 1-(2-methoxyethyl)-1H-pyrazol-4-amino hydrochloride (0.05 g), DIEA (0.12 g) and 10 mL IPA were added to a 25 ml eggplant-shaped flask for reflux reaction for 6 h. At the end of the reaction, the flask was cooled to room temperature to separate out a crystal, and the crystal was subjected to suction filtration under reduced pressure to obtain a title compound.

MS(ESI$^+$): [M+H]$^+$ 395.2.

C) 1-(3-Aminobenzyl)-N-(1-(2-methoxyethyl)-1H-pyrazol-4-yl)-1H-pyrazolo[3,4-d]pyrimidine-6-amino N-(1-(2-methoxyethyl)-1H-pyrazol-4-yl)-1-(3-nitrobenzyl)-1H-pyrazolo[3,4-d]pyrimidine-6-amino (0.2 g), 0.04 g Pd/C and 10 mL EtOH were added to a two-necked flask, and heated to reflux under N$_2$ protection; then 85% hydrazine hydrate (0.57 g) was added dropwisely within 30 min for reaction for 2 h after dropwise adding. At the end of the reaction, the title compound was obtained by filtration under reduced pressure with diatomite and drying under reduced pressure after cooling to room temperature.

MS(ESI$^+$): [M+H]$^+$ 365.2.

D) N-(3-((6-((1-(2-methoxy-ethyl)-1H-pyrazol-4-yl)amino)-1H-pyrazolo[3,4-d]pyrimidine-1-yl)methyl)phenyl)acrylamide 1-(3-aminobenzyl)-N-(1-(2-methoxyethyl)-1H-pyrazol-4-yl)-1H-pyrazolo[3,4-d]pyrimidine-6-amino (0.03 g) and 10 mL dry THF were added to a two-necked flask; and acryloyl chloride (0.008 g) diluted by 2 mL dry THF was added dropwisely at −5° C. under N$_2$ protection for reaction for 2 h at 0° C. after dropwise adding; at the end of the reaction, a saturated NaHCO$_3$ solution was added to regulate PH to be alkaline, then 50 mL×3 EA was added; and organic layers were combined and washed by a saturated salt solution, organic phases were dried by adding anhydrous Na$_2$SO$_4$, and subjected to drying under reduced pressure to obtain the title compound.

MS(ESI$^+$): [M+H]$^+$ 419.2.

Examples 2 to 7

In examples 2 to 7, based on the method the same as that in example 1, the title compound was obtained by 6-chloro-1-(3-nitrobenzyl)-1H-pyrazolo[3,4-d]pyrimidine obtained in step A of example 1 and phenyl optionally substituted by 1 to 3 substituents selected from: halogen atom, cyano, amino, 2-cyanoacetyl, C$_{1-6}$ alcohol, C$_{1-6}$ alcohol ether, C$_{1-6}$ alkyl, C$_{2-8}$ cycloalkylalkyl, C$_{2-6}$ alkenyl and C$_{2-6}$ alkynyl, and the like, or aromatic 5- to 6-membered heterocyclyl (such as, pyrazol, substituted benzene ring) (corresponding to the compounds in examples 2 to 7 to obtain the title compound. MS in the table referred to a measured value.

TABLE 1

| Example No. | IOPAC title | Structural formula | MS |
|---|---|---|---|
| 2 | N-(3-((6-((1-methyl-1H-pyrazol-4-yl)-1H-pyrazolo[3,4-d]pyrimidine-1-yl)methyl)phenyl)acrylamide | | 375.2 |
| 3 | N-(3-((6-((1-(2-hydroxyethyl)-1H-pyrazol-4-yl)amino)-1H-pyrazolo[3,4-d]pyrimidin-1-yl)methyl)phenyl)acrylamide | | 405.2 |
| 4 | N-(3-((6-aniline-1H-pyrazolo[3,4-d]pyrimidin-1-yl)methyl)phenyl)acrylamide | | 371.3 |
| 5 | N-(3-((6-((4-fluorophenyl)amino)-1H-pyrazolo[3,4-d]pyrimidin-1-yl)methyl)phenyl)acrylamide | | 389.3 |

TABLE 1-continued

| Example No. | IOPAC title | Structural formula | MS |
|---|---|---|---|
| 6 | N-(3-((6-((4-morpholinylphenyl)amino)-1H-pyrazolo[3,4-d]pyrimidin-1-yl)methyl)phenyl)acrylamide | | 456.3 |
| 7 | N-(3-((6-((4-(4-methylpiperazin-1-yl)phenyl)amino)-1H-pyrazolo[3,4-d]pyrimidin-1-yl)methyl)phenyl)acrylamide; | | 469.3 |

Embodiment 8

N-(3-((6-((1-(2-methoxy-ethyl)-1H-pyrazol-4-yl)amino)-1H-pyrazolo[3,4-d]pyrimidine-1-yl)methyl)phenyl)but-2-enamide

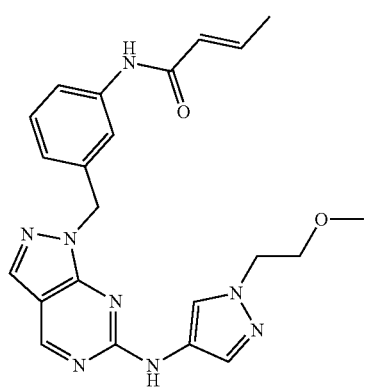 [SMILES: C/C=C/C(=O)Nc1cccc(Cn2ncc3cnc(Nc4cnn(CCOC)c4)nc32)c1]

A) 6-chloro-1-(3-nitrobenzyl)-1H-pyrazolo[3,4-d]pyrimidine 4,6-Dichloro-pyrimidine-5-formaldehyde (8.4 g) and 240 mL THF were added to a 500 ml three-necked flask, and Net3$_3$ (14.56 g) was added at 0° ° C., where the temperature was not greater than 0° C., and stirred for 10 min after dropwise adding, then, 3-nitrylbenzylhydrazine hydrochloride (9.74 g) was added slowly, where the temperature was controlled within 0°C during adding process, and stirred for reaction for 1-2 h after feeding; at the end of the reaction, drying under reduced pressure was performed to obtain a crude product, and the crude product was stirred, separated and purified by silica gel column chromatography to obtain a title compound.

MS(ESI$^+$): [M+H]$^+$ 290.2.

B) N-(1-(2-methoxyethyl)-1H-pyrazol-4-yl)-1-(3-nitrobenzyl)-1H-pyrazolo[3,4-d]pyrimidine-6-amino 6-chloro-1-(3-nitrobenzyl)-1H-pyrazolo[3,4-d]pyrimidine (0.1 g), 1-(2-methoxyethyl)-1H-pyrazol-4-amino hydrochloride (0.05 g), DIEA (0.12 g) and 10 mL IPA were added to a 25 ml eggplant-shaped flask for reflux reaction for 6 h. At the end of the reaction, the title compound was obtained by cooling to room temperature, separating out a crystal and suction filtration under reduced pressure.

MS(ESI$^+$): [M+H]$^+$ 395.2.

C) 1-(3-aminobenzyl)-N-(1-(2-methoxyethyl)-1H-pyrazol-4-yl)-1H-pyrazolo[3,4-d]pyrimidine-6-amino N-(1-(2-methoxyethyl)-1H-pyrazol-4-yl)-1-(3-nitrobenzyl)-1H-pyrazolo[3,4-d]pyrimidine-6-amino (0.2 g), 0.04 g Pd/C and 10 mL EtOH were added to a two-necked flask, and heated to reflux under N$_2$ protection; then 85% hydrazine hydrate (0.57 g) was added dropwisely within 30 min for reaction for 2 h after dropwise adding. At the end of the reaction, the title compound was obtained by cooling to room temperature, filtration under reduced pressure with diatomite and drying under reduced pressure.

MS(ESI$^+$): [M+H]$^+$ 365.2.

D) N-(3-((6-((1-(2-hydroxy-ethyl)-1H-pyrazol-4-yl)amino)-1H-pyrazolo[3,4-d]pyrimidin-1-yl)methyl)phenyl)but-2-enamide 1-(3-aminobenzyl)-N-(1-(2-methoxyethyl)-1H-pyrazol-4-yl)-1H-pyrazolo[3,4-d]pyrimidine-6-amino (0.03 g), and 10 mL dry THF were added to a two-necked flask; crotonyl chloride (0.009 g) diluted by 2 mL dry THF was added dropwisely for reaction for 2 h at 0° C. after dropwise adding; at the end of the reaction, a saturated NaHCO$_3$ solution was added to regulate PH to be alkaline, and 50 mL×3 EA was added, then organic layers were combined and washed by saturated salt solution; and organic phases were dried by adding anhydrous Na$_2$SO$_4$, and subjected to drying under reduced pressure to obtain the title compound. MS(ESI$^+$): [M+H]$^+$ 433.3.

Examples 9 to 14

In examples 9 to 14, based on the method the same as that in example 8, the title compound was obtained by 6-chloro-1-(3-nitrobenzyl)-1H-pyrazolo[3,4-d]pyrimidine obtained in step A of example 8 and phenyl optionally substituted by 1 to 3 substituents selected from: halogen atom, cyano, amino, 2-cyanoacetyl, C$_{1-6}$ alcohol, C$_{1-6}$ alcohol ether, C$_{1-6}$ alkyl, C$_{2-8}$ cycloalkylalkyl, C$_{2-6}$ alkenyl and C$_{2-6}$ alkynyl, and the like, or aromatic 5- to 6-membered heterocyclyl (such as, pyrazol, substituted benzene ring) (corresponding to the compounds in examples 9 to 14). MS in the table referred to a measured value.

TABLE 2

| Example No. | IOPAC title | Structural formula | MS |
|---|---|---|---|
| 9 | N-(3-((6-((1-methyl-1H-pyrazol-4-yl)amino)-1H-pyrazolo[3,4-d]pyrimidin-1-yl)methyl)phenyl)but-2-enamide; | | 389.2 |
| 10 | N-(3-((6-((1-(2-hydroxyethyl)-1H-pyrazol-4-yl)amino)-1H-pyrazolo[3,4-d]pyrimidin-1-yl)methyl)phenyl)but-2-enamide; | | 419.2 |
| 11 | N-(3-((6-aniline-1H-pyrazolo[3,4-d]pyrimidin-1-yl)methyl)phenyl)but-2-enamide | | 385.2 |

TABLE 2-continued
| Example No. | IOPAC title | Structural formula | MS |
|---|---|---|---|
| 12 | N-(3-((6-((4-fluorophenyl)amino)-1H-pyrazolo[3,4-d]pyrimidin-1-yl)methyl)phenyl)but-2-enamide | 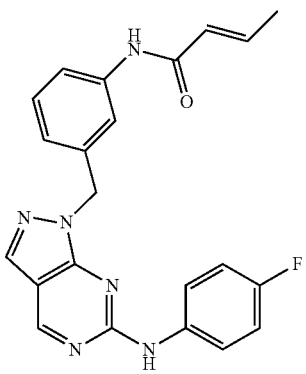 [SMILES: C/C=C/C(=O)Nc1cccc(Cn2ncc3cnc(Nc4ccc(F)cc4)nc32)c1] | 403.2 |
| 13 | N-(3-((6-((4-morpholinylphenyl)amino)-1H-pyrazolo[3,4-d]pyrimidin-1-yl)methyl)phenyl)but-2-enamide; | 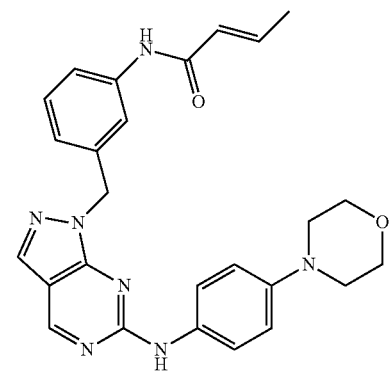 [SMILES: C/C=C/C(=O)Nc1cccc(Cn2ncc3cnc(Nc4ccc(N5CCOCC5)cc4)nc32)c1] | 470.2 |
| 14 | N-(3-((6-((4-(4-methylpiperazin-1-yl)phenyl)amino)-1H-pyrazolo[3,4-d]pyrimidin-1-yl)methyl)phenyl)but-2-enamide; | 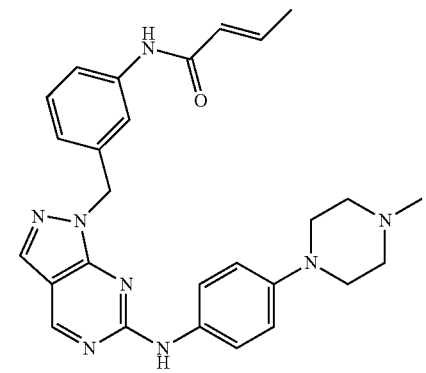 [SMILES: C/C=C/C(=O)Nc1cccc(Cn2ncc3cnc(Nc4ccc(N5CCN(C)CC5)cc4)nc32)c1] | 483.3 |

Embodiment 15

N-(4-((6-((1-(2-methoxyethyl)-1H-pyrazol-4-yl)amino)-1H-pyrazolo[3,4-d]pyrimidine-1-yl)methyl)phenyl)acrylamide

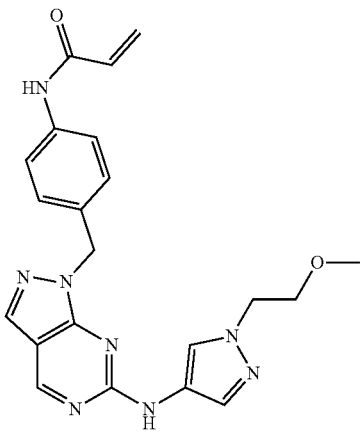 [SMILES: C=CC(=O)Nc1ccc(Cn2ncc3cnc(Nc4cnn(CCOC)c4)nc32)cc1]

A) 6-chloro-1-(4-nitrobenzyl)-1H-pyrazolo[3,4-d]pyrimidine 4,6-Dichloro-pyrimidine-5-formaldehyde (8.4 g) and 240 mL THF were added to a 500 ml three-necked flask, and Net3₃ (14.56 g) was added at 0°C, where the temperature was not greater than 0° C., and stirred for 10 min after dropwise adding, then, 4-nitrylbenzylhydrazine hydrochloride (9.74 g) was added slowly, where the temperature was controlled within 0°C during the adding process, and stirred for reaction for 1-2 h after feeding; at the end of the reaction, drying under reduced pressure was performed to obtain a crude product; a sample was mixed, stirred, separated and purified by silica gel column chromatography to obtain a title compound.
MS(ESI⁺): [M+H]⁺ 290.2.

B) N-(1-(2-methoxyethyl)-1H-pyrazol-4-yl)-1-(4-nitrobenzyl)-1H-pyrazolo[3,4-d]pyrimidine-6-amino 6-Chloro-1-(4-nitrobenzyl)-1H-pyrazolo[3,4-d]pyrimidine (0.1 g), 1-(2-methoxyethyl)-1H-pyrazol-4-amino hydrochloride (0.05 g), DIEA (0.12 g) and 10 mL IPA were added to a 25 ml eggplant-shaped flask for reflux reaction for 6 h. At the end of the reaction, the title compound was obtained by cooling to room temperature, separating out a crystal, and suction filtration under reduced pressure.
MS(ESI⁺): [M+H]⁺ 395.2.

C) 1-(4-aminobenzyl)-N-(1-(2-methoxyethyl)-1H-pyrazol-4-yl)-1H-pyrazolo[3,4-d]pyrimidine-6-amino N-(1-(2-methoxyethyl)-1H-pyrazol-4-yl)-1-(4-nitrobenzyl)-1H-pyrazolo[3,4-d]pyrimidine-6-amino (0.2 g), 0.04 g Pd/C and 10 mL EtOH were added to a two-necked flask, and heated to reflux under N₂ protection; then 85% hydrazine hydrate (0.57 g) was added dropwisely within 30 min for reaction for 2 h after dropwise adding. At the end of the reaction, the title compound was obtained by cooling to room temperature, performing filtration under reduced pressure with diatomite and drying under reduced pressure.
MS(ESI⁺): [M+H]⁺ 365.2.

D) N-(4-((6-((1-(2-methoxy-ethyl)-1H-pyrazol-4-yl)amino)-1H-pyrazolo[3,4-d]pyrimidine-1-yl)methyl)phenyl)acrylamide 1-(4-aminobenzyl)-N-(1-(2-methoxyethyl)-1H-pyrazol-4-yl)-1H-pyrazolo[3,4-d]pyrimidine-6-amino (0.03 g) and 10 mL dry THF were added to a two-necked flask; and acryloyl chloride (0.008 g) diluted by 2 mL dry THF was added dropwisely at −5° C. under N₂ protection for reaction for 2 h at 0° C. after dropwise adding; at the end of the reaction, a saturated NaHCO₃ solution was added to regulate PH to be alkaline, then 50 mL×3 EA was added; and organic layers were combined and washed by a saturated salt solution, organic phases were dried by adding anhydrous Na₂SO₄, and subjected to drying under reduced pressure to obtain the title compound.
MS(ESI⁺): [M+H]⁺ 419.2.

Examples 16 to 21

In examples 16 to 21, based on the method the same as that in example 15, the title compound was obtained by 6-chloro-1-(4-nitrobenzyl)-1H-pyrazolo[3,4-d]pyrimidine obtained in step A of example 15 and phenyl optionally substituted by 1 to 3 substituents selected from: halogen atom, cyano, amino, 2-cyanoacetyl, C₁₋₆ alcohol, C₁₋₆ alcohol ether, C₁₋₆ alkyl, C₂₋₈ cycloalkylalkyl, C₂₋₆ alkenyl and C₂₋₆ alkynyl, and the like, or aromatic 5- to 6-membered heterocyclyl (such as, pyrazol, substituted benzene ring) (corresponding to the compounds in examples 16 to 21). MS in the table referred to a measured value.

TABLE 3

| Example No. | IOPAC title | Structural formula | MS |
|---|---|---|---|
| 16 | N-(4-((6-((1-methyl-1H-pyrazol-4-yl)amino)-1H-pyrazolo[3,4-d]pyrimidine-1-yl)methyl)phenyl)acrylamide | | 375.2 |

TABLE 3-continued

| Example No. | IOPAC title | Structural formula | MS |
|---|---|---|---|
| 17 | N-(4-((6-((1-(2-hydroxyethyl)-1H-pyrazol-4-yl)amino)-1H-pyrazolo[3,4-d]pyrimidin-1-yl)methyl)phenyl)acrylamide; | | 405.2 |
| 18 | N-(4-((6-aniline-1H-pyrazolo[3,4-d]pyrimidin-1-yl)methyl)phenyl)acrylamide | | 371.3 |
| 19 | N-(4-((6-((4-fluorophenyl)amino)-1H-pyrazolo[3,4-d]pyrimidin-1-yl)methyl)phenyl)acrylamide | | 389.3 |

TABLE 3-continued

| Example No. | IOPAC title | Structural formula | MS |
|---|---|---|---|
| 20 | N-(4-((6-((4-morpholinylphenyl)amino)-1H-pyrazolo[3,4-d]pyrimidin-1-yl)methyl)phenyl)acrylamide | | 456.3 |
| 21 | N-(4-((6-((4-(4-methylpiperazin-1-yl)phenyl)amino)-1H-pyrazolo[3,4-d]pyrimidin-1-yl)methyl)phenyl)acrylamide | | 469.3 |

Embodiment 22

N-(4-((6-((1-(2-methoxy-ethyl)-1H-pyrazol-4-yl)amino)-1H-pyrazolo[3,4-d]pyrimidine-1-yl)methyl)phenyl)but-2-enamide

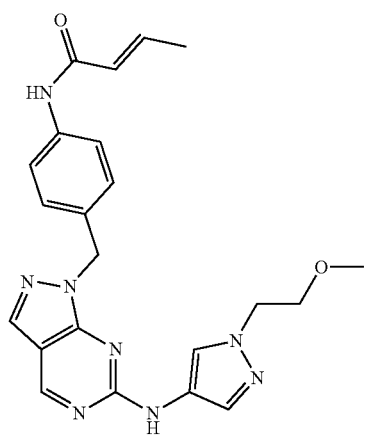 [SMILES: C/C=C/C(=O)Nc1ccc(Cn2ncc3cnc(Nc4cnn(CCOC)c4)nc32)cc1]

A) 6-chloro-1-(4-nitrobenzyl)-1H-pyrazolo[3,4-d]pyrimidine 4,6-Dichloro-pyrimidine-5-formaldehyde (8.4 g) and 240 mL THF were added to a 500 ml three-necked flask, and Net33 (14.56 g) was added at 0°C, where the temperature was not greater than 0° C., and stirred for 10 min after dropwise adding, then, 4-nitrylbenzylhydrazine hydrochloride (9.74 g) was added slowly, where the temperature was controlled within 0° C. during the adding process, and stirred for reaction for 1-2 h after feeding; at the end of the reaction, drying under reduced pressure was performed to obtain a crude product; a sample was mixed, stirred, separated and purified by silica gel column chromatography to obtain a title compound.

MS(ESI⁺): [M+H]⁺ 290.2.

B)N-(1-(2-methoxyethyl)-1H-pyrazol-4-yl)-1-(4-nitrobenzyl)-1H-pyrazolo[3,4-d]pyrimidine-6-amino 6-chloro-1-(4-nitrobenzyl)-1H-pyrazolo[3,4-d]pyrimidine (0.1 g), 1-(2-methoxyethyl)-1H-pyrazol-4-amino hydrochloride (0.05 g), DIEA (0.12 g) and 10 mL IPA were added to a 25 ml eggplant-shaped flask for reflux reaction for 6 h. After the reaction, the flask was cooled to room temperature to separate out a crystal, and the crystal was subjected to suction filtration under reduced pressure to obtain the title compound.

MS(ESI⁺): [M+H]⁺ 395.2.

C) 1-(4-Aminobenzyl)-N-(1-(2-methoxyethyl)-1H-pyrazol-4-yl)-1H-pyrazolo[3,4-d]pyrimidine-6-amino N-(1-(2-Methoxyethyl)-1H-pyrazol-4-yl)-1-(4-nitrobenzyl)-1H-pyrazolo[3,4-d]pyrimidine-6-amino (0.2 g), 0.04 g Pd/C and 10 mL EtOH were added to a two-necked flask, and heated to reflux under N₂ protection; then 85% hydrazine hydrate (0.57 g) was added dropwisely within 30 min for reaction for 2 h after dropwise adding. After the reaction, the title compound was obtained by cooling to room temperature, and performing filtration under reduced pressure with diatomite and drying under reduced pressure.

MS(ESI⁺): [M+H]⁺ 365.2.

D) N-(4-((6-((1-(2-methoxy-ethyl)-1H-pyrazol-4-yl)amino)-1H-pyrazolo[3,4-d]pyrimidine-1-yl)methyl)phenyl)but-2-enamide 1-(4-Aminobenzyl)-N-(1-(2-methoxyethyl)-1H-pyrazol-4-yl)-1H-pyrazol[3,4-d]pyrimidine-6-amino (0.03 g), and 10 mL dry THF were added to a two-necked flask; crotonyl chloride (0.009 g) diluted by 2 mL dry THF was added dropwisely for reaction for 2 h at 0° C. after dropwise adding; after the reaction, a saturated NaHCO₃ solution was added to regulate PH to be alkaline, and 50 mL×3 EA was added, then organic layers were combined and washed by saturated salt solution; and organic phases were dried by adding anhydrous Na₂SO₄, and subjected to drying under reduced pressure to obtain the title compound.

MS(ESI⁺): [M+H]⁺ 433.3.

Examples 23 to 28

In examples 23 to 28, based on the method the same as that in example 22, the title compound was obtained by 6-chloro-1-(4-nitrobenzyl)-1H-pyrazolo[3,4-d]pyrimidine obtained in step A of example 22 and phenyl optionally substituted by 1 to 3 substituents selected from: halogen atom, cyano, amino, 2-cyanoacetyl, $C_{1-6}$ alcohol, $C_{1-6}$ alcohol ether, $C_{1-6}$ alkyl, $C_{2-8}$ cycloalkylalkyl, $C_{2-6}$ alkenyl and $C_{2-6}$ alkynyl, and the like, or aromatic 5- to 6-membered heterocyclyl (such as, pyrazol, substituted benzene ring) (corresponding to the compounds in examples 23 to 28). MS in the table referred to a measured value.

TABLE 4

| Example No. | IOPAC title | Structural formula | MS |
| --- | --- | --- | --- |
| 23 | N-(4-((6-((1-methyl-1H-pyrazol-4-yl)amino)-1H-pyrazolo[3,4-d]pyrimidin-1-yl)methyl)phenyl)but-2-enamide | | 389.2 |
| 24 | N-(4-((6-((1-(2-hydroxyethyl)-1H-pyrazol-4-yl)amino)-1H-pyrazolo[3,4-d]pyrimidin-1-yl)methyl)phenyl)but-2-enamide | | 419.2 |

TABLE 4-continued
| Example No. | IOPAC title | Structural formula | MS |
|---|---|---|---|
| 25 | N-(4-((6-aniline-1H-pyrazolo[3,4-d]pyrimidin-1-yl)methyl)phenyl)but-2-enamide | 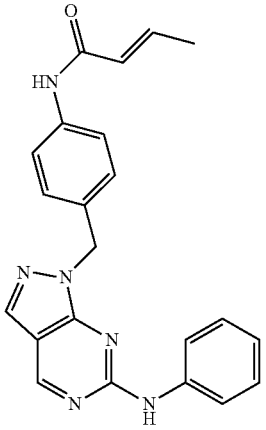 [SMILES: C/C=C/C(=O)Nc1ccc(Cn2ncc3cnc(Nc4ccccc4)nc32)cc1] | 385.2 |
| 26 | N-(4-((6-((4-fluorophenyl)amino)-1H-pyrazolo[3,4-d]pyrimidine-1-yl)methyl)phenyl)but-2-enamide | 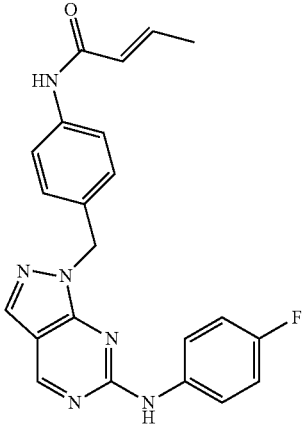 [SMILES: C/C=C/C(=O)Nc1ccc(Cn2ncc3cnc(Nc4ccc(F)cc4)nc32)cc1] | 403.2 |
| 27 | N-(4-((6-((4-morpholinylphenyl)amino)-1H-pyrazolo[3,4-d]pyrimidin-1-yl)methyl)phenyl)but-2-enamide | 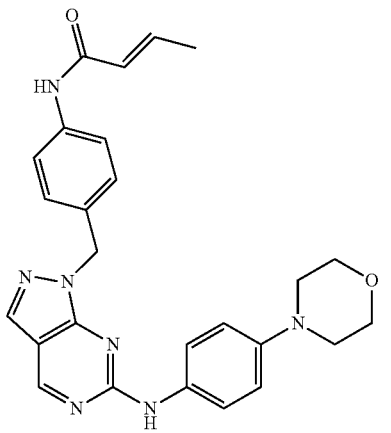 [SMILES: C/C=C/C(=O)Nc1ccc(Cn2ncc3cnc(Nc4ccc(N5CCOCC5)cc4)nc32)cc1] | 470.2 |

TABLE 4-continued

| Example No. | IOPAC title | Structural formula | MS |
|---|---|---|---|
| 28 | N-(4-((6-((4-(4-methylpiperazin-1-yl)phenyl)amino)-1H-pyrazolo[3,4-d]pyrimidin-1-yl)methyl)phenyl)but-2-enamide | | 483.3 |

Experiment Example (Inhibition Tests on JAK-1, JAK-2 and JAK-3 Kinases)

Experimental Goal

To evaluate the inhibitory activity of the compound on JAK-1, JAK-2 and JAK-3 kinases Experimental Principle A proteolytic enzyme is coupled to exert different proteolysis on a specific phosphorylated and nonphosphorylated peptide substrate based on fluorescence resonance energy transfer (FRET). Both ends of the peptide substrate were respectively labeled FRET energy donor coumarin and energy receptor fluorescein, and at this time, the donor was stimulated to produce energy transfer when the donor is close to a receptor.

In Kinase Reaction, JAK-1, JAK-2 or JAK-3 may transfer γ-phosphoric acid in ATP onto a single tyrosine residue of a peptide substrate; and there were JAK-1, JAK-2 or JAK-3 inhibitors in the system, γ-phosphoric acid groups on ATP would be not transferred onto the peptide substrate, thus resulting in the failure of phosphorylation. An evaluation experiment was designed based on the principle, a peptide substrate was designed with kinase phosphorylation sites, namely, protein restriction enzyme cutting sites; and both ends thereof were respectively connected with 2 fluorophores as a donor and a receptor respectively; if the kinase kept activity in the system, a γ-phosphonic acid group was transferred onto restriction enzyme cutting sites of the substrate, so that the γ-phosphonic acid group would not be cut and separated into two segments by a protease; moreover, under the stimulation of a laser having a specific wavelength, energy from a segment of fluorescence would be transferred onto another end of fluorophores, thus emitting energy. Otherwise, after kinase activity was inhibited, phosphoric acid groups would be not transferred, and restriction enzyme cutting sites in the substrate would be cut by a kinase in the system to separate the substrate into two segments, thereby no energy transfer of fluorescence occurred. Based on this, the activity of the kinase was evaluated.

Experimental Procedure

In this experiment, a 10 μl kinase reaction system was selected, firstly, 2.5 μl kinase (concentration: 1 nM), 2.5 μl peptide substrate (concentration: 2 μM), 2.5 μl ATP (concentration: 10 PM) and 2.5 μl compound were added to each system for reaction for 1 h at room temperature, and then a 5 μl test solution was added for reaction for 1 h at room temperature, then a 5 μl stop buffer was added. A microplate reader (Synergy H1, BioTek, USA) was used to measure fluorescence intensity (emission intensity of coumarin at 445 nm and emission intensity of fluorescein at 520 nm were detected under the stimulation of 400 nm). The inhibitory activity of each compound was calculated, where it was believed that fluorescence intensity of a well not containing the kinase was 100% inhibited.

TABLE 5

| Example No. | $IC_{50}$ (nM) | | |
|---|---|---|---|
| | JAK-1 | JAK-2 | JAK-3 |
| 1 | 1051.2 | 747.3 | 1.4 |
| 2 | 1390.0 | 940.6 | 2.2 |
| 3 | 828.7 | 4217.0 | 0.13 |
| 4 | 901.2 | 1120.2 | 1.1 |
| 5 | 1583.7 | 1803.0 | 3.7 |
| 6 | 1001.0 | 3102.0 | 0.10 |
| 7 | 942.3 | 1083.2 | 6.1 |
| 8 | 701.0 | 610.5 | 3.0 |
| 9 | 618.2 | 860.5 | 2.1 |
| 10 | 940.3 | 960.2 | 0.7 |
| 11 | 830.0 | 690.0 | 1.4 |
| 12 | 1030.0 | 2310.5 | 0.2 |
| 13 | 890.3 | 709.5 | 0.4 |
| 14 | 274.2 | 1310.5 | 0.9 |
| 15 | 1542.0 | 602.1 | 0.5 |
| 16 | 1410.6 | 770.3 | 1.4 |
| 17 | 1420.3 | 846.2 | 2.0 |
| 18 | 1991.2 | 1280.1 | 2.8 |
| 19 | 1583.7 | 1803.0 | 3.7 |
| 20 | 934.2 | 892.4 | 1.7 |
| 21 | 2852.0 | 1804.0 | 0.2 |
| 22 | 918.2 | 1246.1 | 2.0 |
| 23 | 940.3 | 696.7 | 0.1 |
| 24 | 1118.2 | 948.4 | 0.2 |
| 25 | 2400.3 | 1036.1 | 1.2 |
| 26 | 880.2 | 803.9 | 0.3 |

TABLE 5-continued

| Example No. | IC$_{50}$ (nM) | | |
|---|---|---|---|
| | JAK-1 | JAK-2 | JAK-3 |
| 27 | 960.3 | 892.8 | 2.0 |
| 28 | 4089.0 | 790.5 | 2.3 |

Formulation Example 1 (Preparation of Tablets)

| | |
|---|---|
| (1) A compound of example 1; | 30 g |
| (2) Lactose; | 50 g |
| (3) Corn starch; | 15 g |
| (4) Calcium carboxymethylcellulose; | 44 g |
| (5) Magnesium stearate; | 1 g |
| | 1000 tablets, 140 g in total |

30 g (1), (2), (3), and (4) in total quantity were stirred with water, dried in vacuum and sieved. The sieved powder was mixed with 14 g (4) and 1 g (5), then a mixture was stamped by a tablet press, thus obtaining 1000 tablets; each tablet contained 30 mg compound of example 1.

Formulation Example 2 (Preparation of Capsules)

| | |
|---|---|
| (1) A compound of example 1; | 30 mg |
| (2) Lactose; | 19 mg |
| (3) Fine powder cellulose; | 10 mg |
| (4) Magnesium stearate; | 1 mg |
| | 60 mg in total |

(1), (2), (3), and (4) were mixed and filled into capsules.

The compound of the present disclosure has excellent selective JAK kinase (Janus Kinase) inhibitory activity, and can be used as a medicament to prevent, treat and/or improve an autoimmune disease (e.g., psoriasis, rheumatoid arthritis, inflammatory bowel disease, Sjogren's syndrome, Behcet's disease, multiple sclerosis, systemic lupus erythematosus and the like).

The invention claimed is:

1. A compound having the following structure or a pharmaceutically acceptable salt thereof:

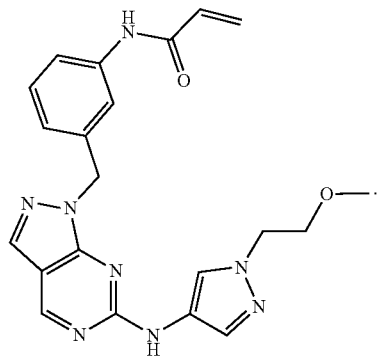 [SMILES: C=CC(=O)Nc1cccc(Cn2ncc3cnc(Nc4cnn(CCOC)c4)nc32)c1]

2. The compound or the pharmaceutically acceptable salt thereof according to claim 1, which is a Janus kinase (JAK) inhibitor.

3. The compound or the pharmaceutically acceptable salt thereof according to claim 2, which is a medicament for treating a JAK-mediated autoimmune disease.

4. The compound or the pharmaceutically acceptable salt thereof according to claim 3, wherein the JAK-mediated autoimmune disease is psoriasis, rheumatoid arthritis, inflammatory bowel disease, Sjogren's syndrome, Behcet's disease, multiple sclerosis or systemic lupus erythematosus.

5. A method for treating a Janus kinase (JAK)-mediated autoimmune disease comprising a step of administering to a subject in need thereof the compound of claim 1 or its pharmaceutically acceptable salt.

6. The method according to claim 5, wherein the JAK-mediated autoimmune disease is selected from the group consisting of psoriasis, rheumatoid arthritis, inflammatory bowel disease, Sjogren's syndrome, Behcet's disease, multiple sclerosis and systemic lupus erythematosus.

* * * * *

UNITED STATES PATENT AND TRADEMARK OFFICE
CERTIFICATE OF CORRECTION

| | | |
|---|---|---|
| PATENT NO. | : 11,993,603 B2 | Page 1 of 1 |
| APPLICATION NO. | : 17/275209 | |
| DATED | : May 28, 2024 | |
| INVENTOR(S) | : Tiantai Zhang et al. | |

It is certified that error appears in the above-identified patent and that said Letters Patent is hereby corrected as shown below:

On the Title Page

Item (72) Inventors should read: Tiantai ZHANG, Beijing (CN); Dayong ZHANG, Nanjing (CN); Chengjuan CHEN, Beijing (CN); Yuan YIN, Nanjing (CN); Runan YU, Nanjing (CN); Lei SHU, Nanjing (CN)

Signed and Sealed this
Twenty-fifth Day of June, 2024

Katherine Kelly Vidal
*Director of the United States Patent and Trademark Office*